US007655645B2

(12) United States Patent
Adam

(10) Patent No.: US 7,655,645 B2
(45) Date of Patent: Feb. 2, 2010

(54) INDOLE DERIVATIVES

(75) Inventor: Julia Adam, Newhouse (GB)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 12/031,851

(22) Filed: Feb. 15, 2008

(65) Prior Publication Data
US 2008/0207598 A1 Aug. 28, 2008

Related U.S. Application Data

(60) Provisional application No. 60/902,736, filed on Feb. 22, 2007.

(30) Foreign Application Priority Data
Feb. 22, 2007 (EP) ................................ 07102870

(51) Int. Cl.
A61K 31/551 (2006.01)
A61K 31/496 (2006.01)
C07D 413/14 (2006.01)
C07D 417/14 (2006.01)

(52) U.S. Cl. .................. 514/218; 514/254.03; 540/575; 544/367

(58) Field of Classification Search ........................ None
See application file for complete search history.

(56) References Cited

U.S. PATENT DOCUMENTS

| 4,939,138 | A | 7/1990 | D'Ambra et al. |
| 2007/0082931 | A1 | 4/2007 | Ratcliffe et al. |
| 2007/0142446 | A1 * | 6/2007 | Adam-Worrall et al. ...... 514/362 |

FOREIGN PATENT DOCUMENTS

| WO | WO 01/58869 A2 | 8/2001 |
| WO | WO 02/36590 A1 | 5/2002 |
| WO | WO 02/060447 A1 | 8/2002 |
| WO | WO 2004/000832 A1 | 12/2003 |
| WO | WO 2005/058327 A1 | 6/2005 |
| WO | WO 2005/089754 A1 | 9/2005 |
| WO | WO 2007/023143 A1 | 3/2007 |
| WO | WO 2008/101995 A1 | 8/2008 |

OTHER PUBLICATIONS

Adam, J., et al., "Recent advances in the cannabinoids", Expert Opinion Ther. Patents, 12(10):1475-1489 (2002).
Eissenstat, M., et al. "Aminoalkylindoles: Structure-Activity Relationships of Novel Cannabinoid Mimetics", J. Med. Chem., 38:3094-3105 (1995).
Howlett, A. C., et. al., "International Union of Pharmacology. XXVII. Classification of Cannabinoid Receptors", Pharmacological Reviews, 54(2):161-202 (2002).
Hwu, J., et al., "Novel Methods for the Synthesis of Functionalized Indoles from Arylhydroxylamines and Activated Acetylenes", J. Org. Chem., 59:1577-1582 (1994).

Iverson, L., et al., "Cannabinoids: a real prospect for pain relief?", Current Opinion in Pharmacology, 2:50-55 (2002).
Jutz, C., "The Vilsmeier-Hack-Arnold Acylations. C-C Bonding-Forming Reactions of Chloromethyleniminium Ions", Advances in Organic Chemistry, 9(Pt1):225-342 (1976).
Miyaura, N., et al., "Palladium-Catalyzed Cross-Coupling Reactions of Organoboron Compounds", Chem. Rev., 95:2457-2483 (1995).
Robinson, S., "Recent Studies on the Fischer Indole Synthesis", Chem. Rev., 69: 227- 250 (1969).
Stratowa, C., et al., "Use of a luciferase reporter system for characterizing G-protein-linked receptors", Current Opinion in Biotechnology, 6:574-581 (1995).
Van Wijngaarden, I., et al., "Development of High-Affinity 5-HT3 Receptor antagonists. Structure-Affinity Relationship of Novel 1,7-Annelated Indole Derivatives. 1", J. Med. Chem., 36:3693-3699 (1993).
PCT International Search Report dated Apr. 23, 2008 and Written Opinion dated Apr. 23, 2008 for corresponding PCT Application No. PCT/EP2008/052141.

* cited by examiner

Primary Examiner—Emily Bernhardt
(74) Attorney, Agent, or Firm—Susan Hess

(57) ABSTRACT

The invention relates to indole derivative having the general Formula I

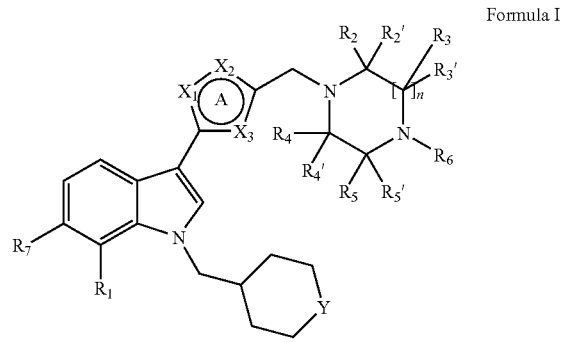

wherein A represents a 5-membered aromatic heterocyclic ring, wherein $X_1$, $X_2$ and $X_3$ are independently selected from N, O, S and CH; Y represents $CH_2$, O, S or $SO_2$; $R_1$ is H, $(C_{1-4})$-alkyl, $(C_{1-4})$alkyloxy, CN or halogen; $R_2$, $R_2'$, $R_3$, $R_3'$, $R_4$, $R_4'$, $R_5$ and $R_5'$ are independently hydrogen, $(C_{1-4})$alkyl (optionally substituted with OH) or CO—$OR_8$; or one pair of geminal substituents $R_3$ and $R_3'$ or $R_5$ and $R_5'$ together represent a keto group, and the others are all hydrogen or $(C_{1-4})$ alkyl; or $R_2$ and $R_5$ together represent a methylene or an ethylene bridge, and $R_2'$, $R_3$, $R_3'$, $R_4$, $R_4'$ and $R_5'$ are hydrogen; n is 1 or 2; $R_6$ is H, $(C_{1-4})$alkyl (optionally substituted with OH, $(C_{1-4})$alkyloxy, CO—$NR_9R_{10}$, CO—$OR_{11}$ or 1,2,4-oxadiazol-3-yl), $SO_2NR_{12}R_{13}$ or $COOR_{14}$; $R_7$ is H or halogen; $R_8$ is $(C_{1-4})$alkyl; $R_9$ and $R_{10}$ are independently hydrogen, $(C_{1-4})$alkyl or $(C_{3-7})$cycloalkyl, the alkyl groups being optionally substituted with OH or $(C_{1-4})$alkyloxy; $R_{11}$ is H or $(C_{1-4})$alkyl; $R_{12}$ and $R_{13}$ are independently H or $(C_{1-4})$alkyl; $R_{14}$ is $(C_{1-6})$alkyl; or a pharmaceutically acceptable salt thereof, as agonists of the cannabinoid CB1 receptor, which can be used in the treatment of pain such as for example peri-operative pain, chronic pain, neuropathic pain, cancer pain and pain and spasticity associated with multiple sclerosis.

21 Claims, No Drawings

INDOLE DERIVATIVES

CROSS REFERENCE TO RELATED APPLICATION

This application claims priority based on U.S. Patent Application No. 60/902,736, filed on Feb. 22, 2007 and European Patent Application No. 07102870.8, filed on Feb. 22, 2007.

FIELD OF THE INVENTION

The present invention relates to indole derivatives, to pharmaceutical compositions comprising the same and to the use of these indole derivatives in therapy, especially in the treatment of pain.

BACKGROUND OF THE INVENTION

Pain treatment is often limited by the side effects of currently available medication. For moderate to severe pain, opioids are widely used. These agents are cheap and effective but suffer from serious and potentially life-threatening side effects, most notably respiratory depression and muscle rigidity. In addition, the doses of opioids which can be administered are limited by nausea, emesis, constipation, pruritus and urinary retention, often resulting in patients electing to receive sub-optimal pain control rather than suffer these distressing side effects. Opioids are highly addictive and are scheduled drugs in many territories. There is therefore a demand for new analgesics that have an improved side effect profile compared to opioids, at equi-analgesic doses. Current treatments for neuropathic pain, including opioids, tricyclic antidepressants, serotonin and noradrenaline uptake inhibitors and anticonvulsants are of limited efficacy. There is therefore a demand for new analgesics that have improved efficacy for the treatment of neuropathic pain.

Evidence is accumulating that cannabinoid agonists have potential as analgesic and anti-inflammatory agents. Two types of cannabinoid receptors are implicated, the cannabinoid CB1 receptor, which is located primarily in the central nervous system but which is also expressed by peripheral neurones and to a lower extent in other peripheral tissues, and the cannabinoid CB2 receptor, which is mostly located in immune cells (Howlett, A. C. et al.: International Union of Pharmacology. XXVII. Classification of Cannabinoid Receptors. *Pharmacol. Rev.* 54, 161-202, 2002). While the CB2 receptor has been implicated in modulating the immune and anti-inflammatory response of cannabinoids, cannabinoid receptor agonists, especially those acting at the CB1 receptor have been suggested as useful in the treatment of pain (see Iversen, L. and Chapman, V. *Current Opinion in Pharmacology,* 2, 50-55, 2002 and references therein). WIN 55, 212-2, the mesylate salt of (R)-(+)-[2,3-dihydro-5-methyl-[(morpholinyl)-methyl]pyrrolo[1,2,3-de]-1,4-benzoxazinyl]-(1-naphthalenyl)methanone was disclosed in U.S. Pat. No. 4,939,138 (Sterling Drug Inc.) as an analgesic agent. The compound is the prototype of aminoalkylindoles (Eissenstat, M. A. et al., *J. Med. Chem.* 38, 3094-3105, 1995), which are potent cannabinoid CB1 receptor agonists that can produce antinociception with equivalent efficacy to morphine in animal models of acute pain, persistent inflammatory pain and neuropathic pain.

Key structural features of aminoalkylindoles having cannabimimetic properties (Adam, J. and Cowley, P. *Expert Opin. Ther. Patents,* 12, 1475-1489, 2002) are an aminoalkyl substituent at the 1-position of the indole moiety, and a further bulky substituent in the 3-position of the indole ring, such as exemplified by an aroyl group in the aminoalkylindoles disclosed in U.S. Pat. No. 4,939,138 (Sterling Drug Inc.) and in the more recent WO02060447 ((University of Connecticut), or by a substituted amido-group in the compounds disclosed in WO0158869 (Bristol-Myers Squibb). 1-(Aminoalkyl)indole derivatives having a substituted oxadiazol-5-yl ring at the 3-position were disclosed in WO0236590 (Amrad Operations PTY Ltd.) as cannabinoid receptor modulators and useful as analgesic agents. In WO2004000832, WO2005058327 and WO2005089754 (Akzo Nobel N.V.), 1-[(indol-3-yl)carbonyl]piperazine derivatives and 1-(indol-3-yl) heterocycle derivatives are disclosed as analgesic agents which modulate the cannabinoid receptor.

There remains a need for cannabinoid agonists with improved properties, such as increased water solubility, for use as therapeutic agents.

SUMMARY OF THE INVENTION

To this end the present invention provides indole derivatives having the general Formula I

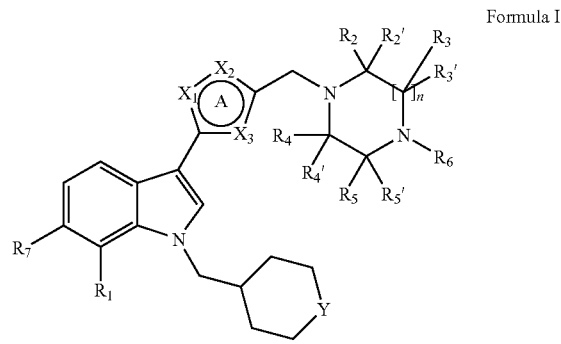

Formula I wherein

A represents a 5-membered aromatic heterocyclic ring, wherein $X_1$, $X_2$ and $X_3$ are independently selected from N, O, S and CH;

Y represents $CH_2$, O, S or $SO_2$;

$R_1$ is H, $(C_{1-4})$alkyl, $(C_{1-4})$alkyloxy, CN or halogen;

$R_2$, $R_2'$, $R_3$, $R_3'$, $R_4$, $R_4'$, $R_5$ and $R_5'$ are independently hydrogen, $(C_{1-4})$alkyl (optionally substituted with OH) or CO—$OR_8$; or one pair of geminal substituents $R_3$ and $R_3'$ or $R_5$ and $R_5'$ together represent a keto group, and the others are all hydrogen or $(C_{1-4})$alkyl; or $R_2$ and $R_5$ together represent a methylene or an ethylene bridge, and $R_2'$, $R_3$, $R_3'$, $R_4$, $R_4'$ and $R_5'$ are hydrogen;

n is 1 or 2;

$R_6$ is H, $(C_{1-4})$alkyl (optionally substituted with OH, $(C_{1-4})$ alkyloxy, CO—$NR_9R_{10}$, CO—$OR_{11}$ or 1,2,4-oxadiazol-3-yl), $SO_2NR_{12}R_{13}$ or $COOR_{14}$;

$R_7$ is H or halogen;

$R_8$ is $(C_{1-4})$alkyl;

$R_9$ and $R_{10}$ are independently hydrogen, $(C_{1-4})$alkyl or $(C_{3-7})$ cycloalkyl, the alkyl groups being optionally substituted with OH or $(C_{1-4})$alkyloxy;

$R_{11}$ is H or $(C_{1-4})$alkyl;

$R_{12}$ and $R_{13}$ are independently H or $(C_{1-4})$alkyl;

$R_{14}$ is $(C_{1-6})$alkyl;

or a pharmaceutically acceptable salt thereof, as agonists of the cannabinoid CB1 receptor, which can be used in the treatment of pain such as for example peri-operative pain, chronic pain, neuropathic pain, cancer pain and pain and spasticity associated with multiple sclerosis.

The indole derivatives of the invention are distinguished from the (indol-3-yl)-heterocycle derivatives disclosed in WO2005089754 (Akzo Nobel N.V.) by the presence of the (homo)piperazine moiety.

DETAILED DESCRIPTION OF THE INVENTION

The 5-membered aromatic heterocyclic ring A, as used in the definition of Formula I, represents a 5-membered aromatic heterocyclic ring, which contains 1-3 heteroatoms selected from N, O and S. This means that at least one of $X_1$, $X_2$ and $X_3$, used to define heterocycle A, cannot be CH. Representative heterocycles A are those derived from thiophene, furan, thiazole, thiadiazole, oxazole, oxadiazole and their isomers including isothiazole, isothiadiazole, isoxazole and isoxadiazole. Preferred heterocycles A are 1,2,4-oxadiazole ($X_1$ is N, $X_2$ is O, $X_3$ is N) and 1,2,4-thiadiazole ($X_1$ is N, $X_2$ is S, $X_3$ is N).

The term $(C_{1-4})$alkyl as used in the definition of Formula I means a branched or unbranched alkyl group having 1-4 carbon atoms, like butyl, isobutyl, tertiary butyl, propyl, isopropyl, ethyl and methyl.

The term $(C_{1-6})$alkyl likewise means a branched or unbranched alkyl group having 1-6 carbon atoms, like hexyl, pentyl, butyl, isobutyl, tertiary butyl, propyl, isopropyl, ethyl and methyl.

The term $(C_{3-7})$cycloalkyl means a cycloalkyl group having 3-7 carbon atoms, like cycloheptyl, cyclohexyl, cyclopentyl, cyclobutyl and cyclopropyl.

In the term $(C_{1-4})$alkyloxy, $(C_{1-4})$alkyl has the meaning as defined above.

The term halogen means F, Cl, Br or I.

The term n can represent the integer 1 or 2, thereby defining piperazine and homopiperazine derivatives of Formula I, respectively. Preferred indole derivatives of the invention are those wherein n is 1.

Indole derivatives of Formula I wherein $R_2$ and $R_5$ together represent a methylene or an ethylene bridge, comprise a bridged piperazine or homopiperazine group, such as for example a 2,5-diazabicyclo[2,2,2]octan-2-yl or a 2,5-diazabicyclo[2.2.1]heptan-2-yl group. There is a preference for indole derivatives according to Formula I, wherein Y is O or $SO_2$. Further preferred are the compounds wherein $R_6$ is $(C_{1-4})$alkyl, substituted with CO—$NR_9R_{10}$ or 1,2,4-oxadiazol-3-yl.

Specifically preferred indole derivatives of the invention are:

3-({5-[4-(carbamoylmethyl)-piperazin-1-yl]methyl}-[1,2,4]-thiadiazol-3-yl)-7-chloro-1-(tetrahydropyran-4-yl)methyl-1H-indole;

7-chloro-3-({5-[4-(ethylcarbamoylmethyl)piperazin-1-yl]methyl}-[1,2,4]-thiadiazol-3-yl)-1-(tetrahydropyran-4-yl)methyl-1H-indole;

7-chloro-3-({5-[4-sulfamoylpiperazin-1-yl]methyl}-[1,2,4]-thiadiazol-3-yl)-1-(tetrahydropyran-4-yl)methyl-1H-indole;

7-ethyl-3-({5-[4-(N-isopropylcarbamoylmethyl)piperazin-1-yl]methyl}-[1,2,4]-thiadiazol-3-yl)-1-(tetrahydropyran-4-yl)methyl-1H-indole;

7-ethyl-3-({5-[4-(methoxycarbonylmethyl)piperazin-1-yl]methyl}-[1,2,4]-thiadiazol-3-yl)-1-(tetrahydropyran-4-yl)methyl-1H-indole;

3-({5-[4-(carbamoylmethyl)piperazin-1-yl]methyl}-[1,2,4]-thiadiazol-3-yl)-7-methoxy-1-(tetrahydropyran-4-yl)methyl-1H-indole;

3-({5-[4-(carbamoylmethyl)piperazin-1-yl]methyl}-[1,2,4]-thiadiazol-3-yl)-7-chloro-1-(1,1-dioxo-hexahydrothiopyran-4-yl)methyl-1H-indole;

3-({5-[4-(carbamoylmethyl)piperazin-1-yl]methyl}-[1,2,4]-oxadiazol-3-yl)-7-chloro-1-(tetrahydropyran-4-yl)methyl-1H-indole;

7-chloro-3-({5-[4-([1,2,4]-oxadiazol-3-ylmethyl)piperazin-1-yl]methyl}-[1,2,4]-oxadiazol-3-yl)-1-(1,1-dioxo-hexahydrothiopyran-4-yl)methyl-1H-indole;

3-[5-[4-(tert-butoxycarbonyl)-cis-2,6-dimethylpiperazin-1-ylmethyl]-[1,2,4]-oxadiazol-3-yl]-7-chloro-1-[(tetrahydropyran-4-yl)methyl]-1H-indole;

3-{5-[4-(carbamoylmethyl)homopiperazin-1-ylmethyl]-[1,2,4]-oxadiazol-3-yl}-7-chloro-1-[(tetrahydropyran-4-yl)methyl]-1H-indole;

(S)-7-chloro-3-[5-[3-hydroxymethyl-4-(methylcarbamoylmethyl)piperazin-1-ylmethyl]-[1,2,4]-oxadiazol-3-yl]-1-[(tetrahydropyran-4-yl)methyl]-1H-indole; and 3-({4-[4-(carbamoylmethyl)piperazin-1-yl]methyl}-[1,3]-thiazol-2-yl)-7-chloro-1-(tetrahydropyran-4-yl)methyl-1H-indole, or a pharmaceutically acceptable salt thereof.

The indole derivatives of the invention may be prepared by methods known in the art of organic chemistry in general.

Indole derivatives of Formula I can for instance be prepared from compounds of Formula II where L is a leaving group, such as a halogen or an alkylsulfonate group, by nucleophilic displacement of the leaving group with an optionally substituted piperazine or homopiperazine of formula

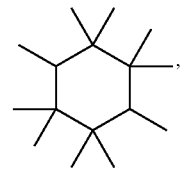

wherein n, $R_2$, $R_2'$, $R_3$, $R_3'$, $R_4$, $R_4'$, $R_5$, $R_5'$ and $R_6$ have the meaning as previously defined. Compounds of Formula II where L is an alkylsulfonate group can be prepared from compounds of Formula II where L is hydroxy, by reaction with an alkylsulfonyl halide in the presence of a base such as triethylamine.

Indole derivatives of Formula I can be prepared from compounds of Formula III by reductive amination, using an optionally substituted piperazine or homopiperazine in the presence of a reducing agent such as sodium triacetoxyborohydride.

It is well known in the art that compounds of Formula II where L is hydroxy can be inter-converted with compounds of Formula III, by oxidation and reduction using suitable oxidising and reducing agents, as described in Burke D. S., Danheiser, R. L. *Handbook of Reagents for Organic Synthesis Oxidising and Reducing agents* (Wiley: New York, 1999). Likewise, compounds of Formula II where L is hydroxy can be prepared from compounds of Formula IV where $R_{15}$ is hydrogen or $(C_{1-4})$alkyl, by reduction using suitable reducing agents.

Formula II

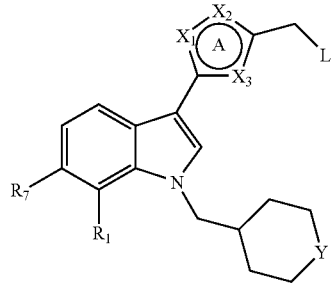

Formula III

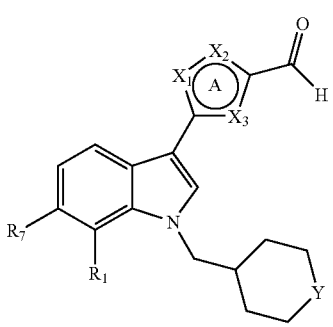

Formula IV

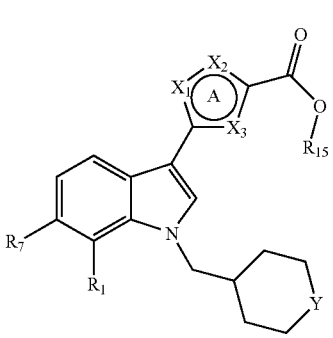

Compounds of Formula I, Formula II, Formula III or Formula IV can be prepared from compounds of Formula V to Formula XII inclusive, using methods well known in the art for constructing heterocyclic rings. Such methods are described in the general reference Katritzky, A. R.: *Comprehensive heterocyclic chemistry* (First Edition, Pergamon Press, 1984, see especially Volume 4, Part 3, *Five-membered rings with one oxygen, sulfur or nitrogen atom* and Volume 6, Part 4B, *Five-membered rings with two or more oxygen, sulfur or nitrogen atoms*).

Formula V

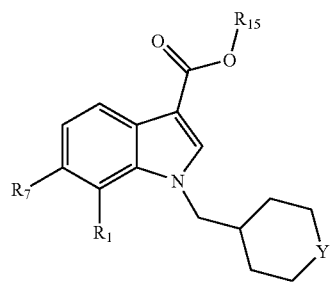

Formula VI

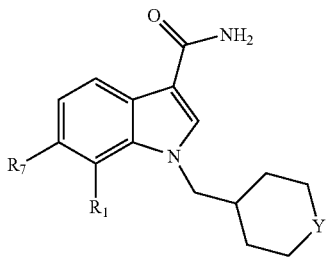

Formula VII

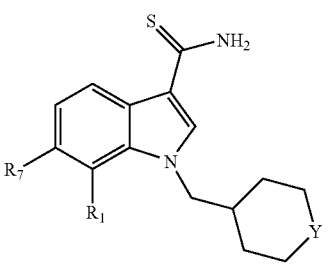

Formula VIII

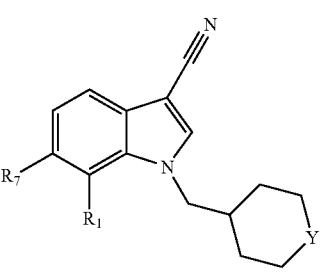

Formula IX

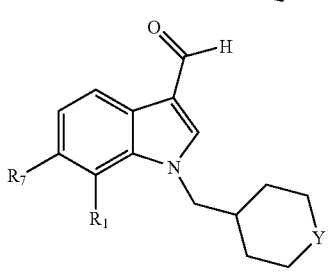

Formula X

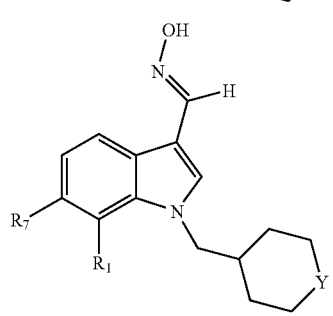

Formula XI

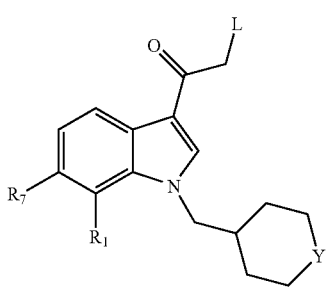

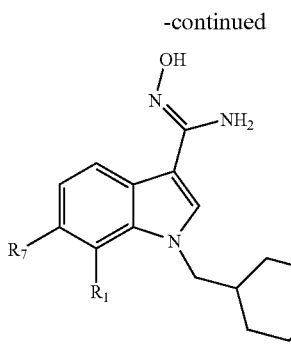

Formula XII

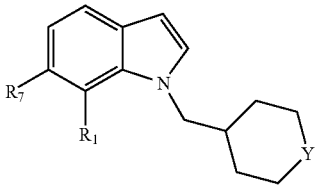

Formula XIII

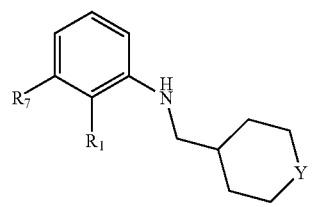

Formula XIV

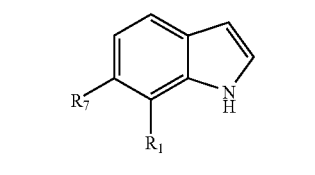

Formula XV

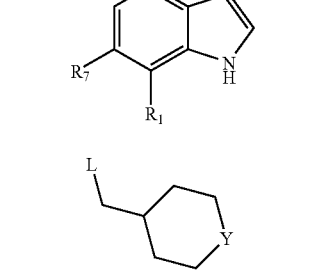

Formula XVI

Compounds of Formula V to Formula XII inclusive, wherein $R_1$, $R_7$, L and Y have the meanings as previously defined and $R_{15}$ is H or $(C_{1-4})$alkyl, can be prepared by literature procedures or modifications of literature procedures known to those persons skilled in the art. For example, compounds of Formula VI can be prepared from compounds of Formula V, or activated derivatives thereof, by reaction with ammonia in a suitable solvent.

Compounds of Formula VII can be prepared from compounds of Formula VI using thionation reagents, such as phosphorus pentasulfide or Lawesson's reagent. Alternatively, compounds of Formula VII can be prepared from compounds of Formula VIII by reaction with thioacetamide in a solvent such as dimethylformamide.

Compounds of Formula VIII can be prepared from compounds of Formula VI by dehydration, for example using trifluoroacetic anhydride in the presence of a base such as triethylamine. Compounds of Formula X can be prepared from compounds of Formula IX by reaction with hydroxylamine in a suitable solvent.

Compounds of Formula XI where L is $NH_2$ can be prepared from compounds of Formula V, or activated derivatives thereof, by reaction with cyanide anion to form an oxoacetonitrile, followed by reduction of the nitrile to a primary amine using a reducing agent, such as hydrogen gas in the presence of a catalyst such as palladium on charcoal.

Compounds of Formula XII can be prepared from compounds of Formula VIII by reaction with hydroxylamine in a suitable solvent.

Compounds of Formula V and compounds of Formula XI can be prepared by acylation of compounds of Formula XIII. For example, compounds of Formula V where $R_{15}$ is hydrogen can be prepared by acylation of compounds of Formula XIII using trifluoroacetic anyhydride in a solvent such as dimethylformamide, followed by hydrolysis using aqueous sodium hydroxide at an elevated temperature. Compounds of Formula XI where L is chlorine can be prepared by acylation of compounds of Formula XIII using chloroacetyl chloride, in the presence of a base such as pyridine.

Compounds of Formula IX can be prepared from compounds of Formula XIII by formylation, for example using the Vilsmeier reaction (for a review see Jutz, C. *Adv. Org. Chem.* 9, pt. 1, 225-342, 1976).

Alternatively, compounds of Formula V can be prepared from compounds of Formula XIV using procedures described by Wijngaarden et al., (*J. Med. Chem.* 36, 3693-3699, 1993) or Hwu et al., (*J. Org. Chem.* 59, 1577-1582, 1994) or modifications of these procedures.

Compounds of Formula XIII can be prepared by literature procedures or modifications of literature procedures known to those persons skilled in the art. For example, compounds of Formula XIII can be prepared by alkylation of compounds of Formula XV, by treatment with a base such as sodium hydride, followed by reaction with an alkylating agent of Formula XVI, where Y has the meaning as defined before and L is a leaving group, such as a halogen or alkylsulfonate group. Compounds of Formula XV can be obtained from commercial sources, prepared by literature procedures or modifications of literature procedures known to those persons skilled in the art.

Alternatively, compounds of Formula XIII can be prepared from compounds of Formula XIV using the Fischer indole synthesis or modifications thereof (*Chem. Rev.* 69, 227-250, 1969). Compounds of Formula XIV can be prepared by literature procedures or modifications of literature procedures known to those persons skilled in the art.

Compounds of Formula I, Formula II, Formula III or Formula IV may alternatively be prepared from compounds of Formula XVII using transition metal catalysed coupling reactions, as described in the general reference Hegedus, L. S. *Transition Metals in the Synthesis of Complex Organic Molecules* (Second Edition, University Science: Sausalito 1999).

For example, compounds of Formula III may be prepared by the reaction of compounds of Formula XVII, where $Y_1$ is halogen, with compounds of Formula XVIII, where $Y_2$ is a boronic acid or a boronic acid ester, using a Suzuki reaction (*Chem. Rev.* 95, 2457-2483, 1995) or a modification thereof.

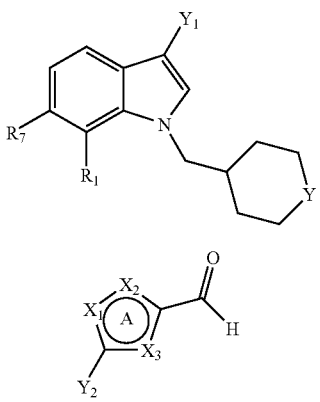

Formula XVII

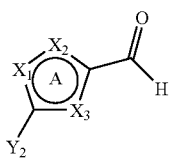

Formula XVIII

Compounds of Formula XVII and compounds of Formula XVIII can be obtained from commercial sources, prepared by literature procedures or modifications of literature procedures known to those persons skilled in the art. For example, compounds of Formula XVII where $Y_1$ is bromine may be prepared by bromination of a compound of Formula XIII using bromine in a solvent such as dimethylformamide.

It will be appreciated by those persons skilled in the art that the indole nitrogen may be temporarily protected during the transformations described above using a protecting group, such as an arylsulfonyl group, to be deprotected and alkylated at a later stage in the synthesis. It will further be appreciated that such protecting groups may be used to modify the stability of intermediates and the reactivity of the indole ring towards electrophiles. Suitable protecting groups are described in Kocienski, P. J.: *Protecting Groups*, Thieme, Stuttgart; New York, 1994.

The skilled person will likewise appreciate that various indole derivatives of Formula I can be obtained by appropriate conversion reactions of functional groups corresponding to certain of the substituents $R_2$-$R_6$.

For example, compounds of Formula I wherein $R_6$ is $(C_{1-4})$alkyl (optionally substituted with OH, $(C_{1-4})$alkyloxy, CO—$NR_9R_{10}$, CO—$OR_{11}$ or 1,2,4-oxadiazol-3-yl), can be prepared by reaction of a compound of Formula I where $R_6$ is hydrogen with a $(C_{1-4})$alkyl halide or a functionalised $(C_{1-4})$ alkyl halide, in the presence of a base such as potassium carbonate. Compounds of Formula I wherein $R_6$ is $SO_2NR_{12}R_{13}$ can be prepared by reaction of a compound of Formula I where $R_6$ is hydrogen with a sulfamide or a functionalised sulfamoyl chloride, in the presence of a base such as pyridine. Compounds of Formula I wherein $R_2$, $R_2'$, $R_3$, $R_3'$, $R_4$, $R_4'$, $R_5$ or $R_5'$ is $CH_2OH$ can be prepared from compounds of Formula I wherein $R_2$, $R_2'$, $R_3$, $R_3'$, $R_4$, $R_4'$, $R_5$ or $R_5'$ is CO—$OR_8$ by reduction using a suitable reducing agent.

The indole derivatives of Formula I and their salts may contain at least one centre of chirality, and exist therefore as stereoisomers, including enantiomers and diastereomers. The present invention includes the aforementioned stereoisomers within its scope and each of the individual R and S enantiomers of the compounds of Formula I and their salts, substantially free, i.e. associated with less than 5%, preferably less than 2%, in particular less than 1% of the other enantiomer, and mixtures of such enantiomers in any proportions including the racemic mixtures containing substantially equal amounts of the two enantiomers. Methods for asymmetric synthesis or chiral separation whereby the pure stereoisomers are obtained are well known in the art, e.g. synthesis with chiral induction or starting from commercially available chiral substrates, or separation of stereoisomers, for example using chromatography on chiral media or by crystallisation with a chiral counter-ion.

Pharmaceutically acceptable salts may be obtained by treating a free base of a compound of Formula I with a mineral acid such as hydrochloric acid, hydrobromic acid, phosphoric acid and sulfuric acid, or an organic acid such as for example ascorbic acid, citric acid, tartaric acid, lactic acid, maleic acid, malonic acid, fumaric acid, glycolic acid, succinic acid, propionic acid, acetic acid and methane sulfonic acid.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising an indole derivative according to general Formula I, or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, epidural, intrathecal, intramuscular, transdermal, pulmonary, local, or rectal administration, and the like, all in unit dosage forms for administration. A preferred route of administration is the oral route.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use. Mixed with such pharmaceutically acceptable auxiliaries, e.g. as described in the standard reference, Gennaro, A. R. et al, Remington: *The Science and Practice of Pharmacy* (20th Edition, Lippincott Williams & Wilkins, 2000, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The indole derivatives of the invention were found to be agonists of the CB1 receptor, as determined in a human CB1 reporter assay using CHO cells. Methods to determine receptor binding as well as in vitro biological activity of cannabinoid receptor modulators are well known in the art. In general, expressed receptor is contacted with the compound to be tested and binding or stimulation or inhibition of a functional response is measured.

To measure a functional response isolated DNA encoding the CB1 receptor gene, preferably the human receptor, is expressed in suitable host cells. Such a cell might be the Chinese Hamster Ovary cell, but other cells are also suitable. Preferably the cells are of mammalian origin.

Methods to construct recombinant CB1 expressing cell lines are well known in the art (Sambrook et al, Molecular Cloning: a Laboratory Manual, Cold Spring Harbor Laboratory Press, Cold Spring Harbor, latest edition). Expression of the receptor is attained by expression of the DNA encoding the desired protein. Techniques for ligation of additional sequences and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then contacted with the test compound to observe binding, or stimulation or inhibition of a functional response.

Alternatively isolated cell membranes containing the expressed CB1 (or CB2) receptor may be used to measure binding of compound.

For measurement of binding radioactively or fluorescently labelled compounds may be used. The most widely used radiolabelled cannabinoid probe is [$^3$H]CP55940, which has approximately equal affinity for CB1 and CB2 binding sites.

Functional CB1 receptor agonist activity may be measured by determining the second messenger response, such as for example measurement of receptor mediated changes in cAMP or MAPkinase pathways. Thus, such a method involves expression of the CB1 receptor on the cell surface of a host cell and exposing the cell to the test compound. The second messenger response is then measured. The level of second messenger will be reduced or increased, depending on the effect of the test compound upon binding to the receptor.

In addition to direct measurement of e.g. cAMP levels in the exposed cell, cells can be used which in addition to transfection with receptor encoding DNA are also transfected with a second DNA encoding a reporter gene, the expression of which correlates with receptor activation. In general, reporter gene expression might be controlled by any response element reacting to changing levels of second messenger. Suitable reporter genes are e.g. LacZ, alkaline phosphatase, firefly luciferase and green fluorescence protein. The principles of such transactivation assays are well known in the art and are described e.g. in Stratowa, C. A. et al., *Curr. Opin. Biotechnol.* 6, 574 (1995). For selecting active agonist compounds on the CB1 receptor the $EC_{50}$ value must be $<10^{-5}$ M, preferably $<10^{-7}$ M.

The compounds may be used as analgesic agents in the treatment of pain such as for example peri-operative pain, chronic pain, neuropathic pain, cancer pain and pain and spasticity associated with multiple sclerosis.

Cannabinoid agonists of the invention would also potentially be useful in the treatment of other disorders including multiple sclerosis, spasticity, inflammation, glaucoma, nausea and emesis, loss of appetite, sleep disturbances, respiratory disorders, allergies, epilepsy, migraine, cardiovascular disorders, neurodegenerative disorders, anxiety, traumatic brain injury and stroke.

The compounds could also be used in conjunction with other drugs, for example analgesic drugs such as opioids and non-steroidal anti-inflammatory drugs (NSAIDs), including COX-2 selective inhibitors.

The compounds of the invention may be administered to humans in a sufficient amount and for a sufficient amount of time to alleviate the symptoms. Illustratively, dosage levels for humans can be in the range of 0.001-50 mg per kg body weight, preferably in a dosage of 0.01-20 mg per kg body weight.

The invention is illustrated by the following Examples.

General Methods

Microwave reactions were performed using an Emrys Optimizer™ (Personal Chemistry) unless otherwise stated.

Flash column chromatography was performed on silica gel.

Semi-preparative high pressure liquid chromatography (semi-prep. HPLC) was performed using the methods outlined below:

Method (i): Waters Xterra (RP18, 5 μm) 30 mm×100 mm; 10-100% acetonitrile-water over a 25 minute gradient; 25 ml/min; 0.1% trifluoroacetic acid buffer; detection by UV at 254 nm.

Method (ii): Waters Xterra (RP18, 5 μm) 30 mm×100 mm; 10-100% acetonitrile-water over a 25 minute gradient; 25 ml/min; 5 mM ammonium bicarbonate buffer, adjusted to pH 10 with ammonia; detection by UV at 254 nm.

$^1$H NMR coupling constants are given in Hz.

Preparation of Intermediates.

I: Toluene-4-sulfonic acid tetrahydropyran-4-ylmethyl ester Intermediate p-Toluenesulfonyl chloride (29.8 g, 157 mmol) was added portionwise to a mixture of tetrahydro-2H-pyran-4-yl-methanol (20.0 g, 172 mmol) and pyridine (25.2 ml, 313 mmol) in dichloromethane (200 ml). The mixture was stirred at room temperature for 17 h, then quenched with aqueous hydrochloric acid (2 M; 100 ml). The layers were separated and the aqueous layer extracted 2 with dichloromethane (2×100 ml). The organic layers were combined and concentrated in vacuo. Recrystallisation from dichloromethane:n-heptane (5:1) afforded toluene-4-sulfonic acid tetrahydro-pyran-4-ylmethyl ester. The mother liquors were further purified by silica gel column chromatography eluting with 50% dichloromethane in n-heptane to yield a further quantity of toluene-4-sulfonic acid tetrahydropyran-4-ylmethyl ester (total yield 41.6 g, 154 mmol).

II: Toluene-4-sulfonic acid 1,1-dioxo-hexahydro-1-thiopyran-4-ylmethyl ester intermediate Step A: Tetrahydro-thiopyran-4-carbonitrile A mixture of tetrahydro-thiopyran-4-one (75 g, 646 mmol) and toluenesulfonylmethyl isocyanide (138.6 g, 710 mmol)

in dimethoxyethane (2.5 L) was cooled to 0° C. and a solution of potassium tert-butoxide (145 g, 1.29 mol) in tert-butanol (1.3 L) added dropwise. The mixture was then allowed to warm to room temperature and stirred for 3 h before dilution with diethyl ether (3 L), washing with saturated sodium bicarbonate (2×1.5 L) and drying over magnesium sulfate. Removal of the solvent in vacuo gave tetrahydro-thiopyran-4-carbonitrile as a pale brown oil (88.3 g, 646 mmol).

Step B: Tetrahydro-thiopyran-4-carboxylic acid

A solution of tetrahydro-thiopyran-4-carbonitrile (646 mmol) in ethanol (600 ml) was added in one portion to a rapidly stirring mixture of sodium hydroxide (258.4 g, 6.46 mol) in water (1.1 L). The mixture was then heated to 90° C. for 2 h, cooled to 0° C. and the pH adjusted to 2 with conc. hydrochloric acid solution. The ethanol was then removed in vacuo and the suspension extracted into dichloromethane (3×1 L). The combined organic extracts were then dried over magnesium sulfate and evaporated in vacuo to give tetrahydro-thio-pyran-4-carboxylic acid as a brown solid (96 g, 646 mmol).

Step C: (Tetrahydro-thiopyran-4-yl)-methanol

A solution of borane dimethylsulfide complex (73.5 ml, 775 mmol) in anhydrous tetrahydrofuran (1.5 L) was treated dropwise over 15 min with a solution of tetrahydro-thiopyran-4-carboxylic acid (646 mmol) in anhydrous tetrahydrofuran (300 ml). The mixture was then heated to 70° C. for 2 h, cooled to room temperature and quenched by dropwise addition of water until effervescence ceased. A further portion of water (500 ml) was then added and the tetrahydrofuran removed in vacuo. The residue was then acidified with dilute hydrochloric acid solution and extracted into dichloromethane (3×500 ml). The combined organic layers were then dried over sodium sulfate and the solvent removed in vacuo to give (tetrahydro-thiopyran-4-yl)-methanol as a brown oil (90.2 g, 646 mmol).

Step D: (1,1-Dioxo-hexahydro-1-thiopyran-4-yl)-methanol

A solution of sodium periodate (304 g, 1.42 mol) in water (3 L) was treated with a solution of (tetrahydro-thiopyran-4-yl)-methanol in methanol (1.7 L) and the mixture heated to 60° C. for 3 h. Sodium periodate (10 g) was then added and heating continued for a further 1 h before removal of all volatiles in vacuo. The resulting granular residue was then shaken with successive portions of diethyl ether (2×500 ml), dichloromethane (2×500 ml) and 50% (v/v) dichloromethane in methanol (2×500 ml). The remaining residue was then treated to a continuous extraction using dichloromethane for 18 h and the solvent combined with the earlier solvent extractions, dried over sodium sulfate and evaporated in vacuo to give (1,1-dioxo-hexahydro-1-thiopyran-4-yl)-methanol as an orange oil (106.2 g, 646 mmol) which crystallised on standing.

Step E: Toluene-4-sulfonic acid 1,1-dioxo-hexahydro-1-thiopyran-4-ylmethyl ester A solution of (1,1-dioxo-hexahydro-1-thiopyran-4-yl)-methanol (105 g, 640 mmol), pyridine (155 ml, 1.92 mol) and 4-dimethylaminopyridine (2.5 g, 20.5 mmol) in chloroform (1.5 L) was treated portionwise with p-toluenesulfonyl chloride (244 g, 1.28 mol) over 15 mins. The mixture was the stirred for 72 h, washed with water (2×1 L), saturated sodium chloride solution (1 L) and dried over sodium sulfate. The organic solvent was removed in vacuo and the oily residue shaken with 60% (v/v) n-heptane in ethyl acetate to give a brown solid on filtration. This was dissolved in the minimum dichloromethane, passed through a celite pad eluting with ethyl acetate (4 L). The solvent was then removed in vacuo until the solution volume was 750 ml and n-heptane (1.5 L) added. The resulting suspension was then filtered to give the title compound as a sandy solid (130 g, 408 mmol). $^1$H NMR (400 MHz, CDCl$_3$): 1.80-2.00 (3H, m), 2.07-2.15 (2H, m), 2.46 (3H, s), 2.90-3.09 (4H, m), 3.90 (2H, d, J 6.3), 7.36 (2H, d, J 8.1) and 7.78 (2H, d, J 8.2).

EXAMPLE 1

3-({5-[4-(Carbamoylmethyl)piperazin-1-yl]methyl}-[1,2,4]-thiadiazol-3-yl)-7-chloro-1-(tetrahydropyran-4-yl)methyl-1H-indole, bis-hydrochloride salt Step A: 7-Chloro-1H-indole-3-carboxylic acid A solution of 7-chloroindole (7.1 g, 47.0 mmol) in dimethylformamide (60 ml) was cooled to 5° C. under nitrogen and trifluoroacetic anhydride (7.6 ml, 54.0 mmol) was added over 10 mins, maintaining the temperature below 10° C. The mixture was stirred at 5-10° C. for 2 h, then poured into water (600 ml). The resulting suspension was stirred for 15 mins and the 7-chloro-3-[(trifluoromethyl)carbonyl]-1H-indole precipitate was filtered off, washing with water to neutrality. The damp solid was suspended in 4 M aqueous sodium hydroxide (500 ml) and heated to reflux with stirring for 1 h. The mixture was cooled and washed with diethyl ether (2×100 ml). The aqueous phase was then acidified to pH 1 using 5 M hydrochloric acid and the resulting fine precipitate filtered off, washed with water to neutrality and dried to afford 7-chloro-1H-indole-3-carboxylic acid as a pink solid (7.5 g, 38.0 mmol).

Step B: 7-Chloro-1-(tetrahydropyran-4-yl)methyl-1H-indole-3-carboxylic acid

To a solution of 7-chloro-1H-indole-3-carboxylic acid (7.5 g, 38.0 mmol) in dimethyl-formamide (100 ml) at 10° C. under nitrogen was added sodium hydride (60% dispersion in mineral oil, 3.1 g, 76.0 mmol) portionwise over 10 mins, maintaining the temperature below 15° C. The cooling bath was removed and the suspension stirred for 90 mins. Toluene-4-sulfonic acid tetrahydropyran-4-ylmethylester (14.6 g, 53.0 mmol) was added. The mixture was heated at 50° C. with stirring for 6 h. Dimethylformamide was removed by evaporation and the residue was dissolved in water (500 ml). The emulsion was washed with dichloromethane (2×100 ml). The aqueous phase was acidified to pH 1 using 5 M hydrochloric acid and the precipitate filtered off, washed with water to neutrality and dried to afford 7-chloro-1-(tetrahydropyran-4-yl)methyl-1H-indole-3-carboxylic acid (15.0 g, 51.0 mmol) as a white solid.

Step C: 7-Chloro-1-(tetrahydropyran-4-yl)methyl-1H-indole-3-carboxylic acid amide Oxalyl chloride (9.0 ml, 102 mmol) was added dropwise to a mixture of 7-chloro-1-(tetrahydropyran-4-yl)methyl-1H-indole-3-carboxylic acid (15.0 g, 51.0 mmol) and dichloromethane (300 ml) under ice-water cooling and the resulting mixture was stirred at room temperature for 18 h. Dichloromethane and excess oxalyl chloride were removed by evaporation and the obtained residue was mixed with dichloromethane (300 ml). Aqueous ammonia solution (200 ml) was added, followed by potassium carbonate (13.5 g, 102 mmol). The resulting mixture was stirred for 1 h. The precipitate was filtered off and dried to afford 7-chloro-1-(tetrahydropyran-4-yl)methyl-1H-indole-3-carboxylic acid amide (8.0 g, 27.0 mmol) as a white solid. The remaining filtrate was washed with water (2×100 ml), dried over sodium sulfate, and concentrated in vacuo, to afford 7-chloro-1-(tetrahydropyran-4-yl)methyl-1H-indole-3-carboxylic acid amide (5.0 g, 17.0 mmol) as a brown solid.

Step D: 7-Chloro-3-([1,3,4]-oxathiazol-2-on-5-yl)-1-(tetrahydropyran-4-yl)methyl-1H-indole To a suspension of 7-chloro-1-(tetrahydropyran-4-yl)methyl-1H-indole-3-carboxylic acid amide (8.0 g, 27.0 mmol) in tetrahydrofuran (100 ml) was added chlorocarbonylsulfenyl chloride (4.7 ml, 55.0 mmol) and the reaction mixture was heated at reflux for 3 h and allowed to cool. The precipitate was filtered off and dried to give 7-chloro-3-([1,3,4]-oxathiazol-2-on-5-yl)-1-(tetrahydropyran-4-yl)methyl-1H-indole (5.3 g, 15.0 mmol) as a white solid. The filtrate was concentrated in vacuo, and the resulting solid was washed with 5% ethyl acetate in n-heptane then dried to afford a further batch of 7-chloro-3-([1,3,4]-oxathiazol-2-on-5-yl)-1-(tetrahydropyran-4-yl)methyl-1H-indole (2.6 g, 7.0 mmol) as a pink solid.

Step E: 7-Chloro-3-({5-ethoxycarbonyl}-([1,2,4]thiadiazol-3-yl))-1-(tetrahydropyran-4-yl)methyl-1H-indole To a suspension of 7-chloro-3-([1,3,4]-oxathiazol-2-on-5-yl)-1-(tetrahydropyran-4-yl)methyl-1H-indole (0.79 g, 2.0 mmol) in m-xylene (10 ml) was added ethylcyanoformate (2.2 ml, 23 mmol) and the reaction subjected to microwave irradiation at 180° C. for 15 mins using an Emrys Optimizer EXP™. The reaction was repeated ten times on the same scale, combined and solvent removed in vacuo to give 7-chloro-3-({5-ethoxycarbonyl}-([1,2,4]thia-diazol-3-yl))-1-(tetrahydropyran-4-yl)methyl-1H-indole (7.1 g, 17 mmol) as a white solid.

Step F: 7-Chloro-3-({5-hydroxymethyl}-([1,2,4]thiadiazol-3-yl))-1-(tetrahydropyran-4-yl)methyl-1H-indole To a cooled solution (ice/methanol bath) of 7-chloro-3-({5-ethoxycarbonyl}-([1,2,4]thiadiazol-3-yl))-1-(tetrahydropyran-4-yl)methyl-1H-indole (7.1 g, 17.0 mmol) in tetrahydrofuran (80 ml) and methanol (80 ml) was added sodium borohydride (1.9 g, 50.0 mmol) portionwise. The reaction was stirred for 18 h and then quenched with 1 M hydrochloric acid (20 ml). The methanol and tetrahydrofuran were removed in vacuo and dichloromethane (200 ml) and 2M hydrochloric acid (50 ml) were added. The organics were separated and washed with brine (50 ml), dried over sodium sulfate and the solvent removed in vacuo. The resulting residue was purified by flash column chromatography eluting with 20%-50% (v/v) ethyl acetate in n-heptane to give 7-chloro-3-({5-hydroxymethyl}-([1,2,4]thiadiazol-3-yl))-1-(tetrahydropyran-4-yl)methyl-1H-indole (3.6 g, 10.0 mmol) as a light pink solid.

Step G: Methanesulfonic acid 3-(1-{tetrahydropyran-4-yl}methyl-7-chloro-1H-indol-3-yl)-[1,2,4]thiadiazol-5-ylmethyl ester To a cooled solution (ice/methanol bath) of 7-chloro-3-({5-hydroxymethyl}-([1,2,4]thiadiazol-3-yl))-1-(tetrahydropyran-4-yl)methyl-1H-indole (3.6 g, 10.0 mmol) in dichloromethane (150 ml) was added methanesulfonyl chloride (0.97 ml, 12.0 mmol) and triethylamine (2.6 ml, 20.0 mmol) sequentially. The reaction was allowed to stir for 1 h and then poured into a separating funnel. The organics were washed with 5% aqueous sodium carbonate solution (2×100 ml), brine (1×100 ml), dried over sodium sulfate and the solvent removed in vacuo to afford methanesulfonic acid 3-(1-{tetrahydropyran-4-yl}methyl-7-chloro-1H-indol-3-yl)-[1,2,4]thiadiazol-5-ylmethyl ester (4.6 g, 10.0 mmol) which was used without further purification.

Step H: 3-[{5-[4-(Carbamoylmethyl)piperazin-1-yl]methyl}-[1,2,4]-thiadiazol-3-yl]-7-chloro-1-(tetrahydropyran-4-yl)methyl-1H-indole, bis-hydrochloride salt To a solution of methanesulfonic acid 3-(1-{tetrahydropyran-4-yl}methyl-7-chloro-1H-indol-3-yl)-[1,2,4]thiadiazol-5-ylmethyl ester (388 mg, 0.88 mmol) in 1-methyl-2-pyrrolidinone (5 ml) was added 2-piperazin-1-ylacetamide (152 mg, 1.06 mmol) and potassium carbonate (174 mg, 1.26 mmol). The reaction was stirred at room temperature for 18 h. The reaction was diluted with dichloromethane (8 ml) and filtered through a 10 g Strata™ SCX giga tube. The tube was washed with methanol and then eluted with 2 M ammonia in methanol. The methanolic ammonia solution was evaporated and the residue purified by HPLC [method (i)]. The product was dissolved in methanol and filtered through a 5 g Strata™ SCX giga tube, eluting with 2 M ammonia in methanol, to afford the title compound as the free base. The free base was dissolved in dichloromethane and hydrogen chloride (2M solution in diethyl ether; 1.0 ml, 2.0 mmol) was added. The mixture was concentrated in vacuo to afford the title compound, (118 mg, 0.21 mmol), as a bis-hydrochloride salt. EsIMS: m/z 491.1, 489.5 [M+H]$^+$.

EXAMPLE 2

7-Chloro-3-({5-[4-(ethoxycarbonyl)methylpiperazin-1-yl]methyl}-[1,2,4]-thiadiazol-3-yl)-1-(tetrahydropyran-4-yl)methyl-1H-indole, trifluoroacetic acid salt To a solution of methanesulfonic acid 3-(1-{tetrahydropyran-4-yl}methyl-7-chloro-1H-indol-3-yl)-[1,2,4]thiadiazol-5-ylmethyl ester (1.5 g, 3.4 mmol) in 1-methyl-2-pyrrolidinone (10 ml) was added N,N-diisopropylethylamine (1.5 ml, 8.5 mmol) and 1-(ethoxycarbonylmethyl)-piperazine (879 mg, 5.1 mmol). The reaction was stirred at room temperature for 18 h. The mixture was then partitioned between water and diethyl ether. The organic layer was separated, dried (MgSO$_4$) and the solvent evaporated to afford 7-chloro-3-[{5-[4-(ethoxycarbonyl)-methylpiperazin-1-yl]methyl}-[1,2,4]-thiadiazol-3-yl]-1-(tetrahydropyran-4-yl)methyl-1H-indole as the free base (1.28 g, 2.5 mmol). An aliquot was purified by HPLC [method (i)] to afford the title compound as a trifluoroacetic acid salt. EsIMS: m/z 518.5 [M+H]$^+$.

EXAMPLE 3

7-Chloro-3-({5-[4-(ethylcarbamoyl)methylpiperazin-1-yl]methyl}-[1,2,4]-thiadiazol-3-yl)-1-(tetrahydropyran-4-yl)methyl-1H-indole 7-Chloro-3-[{5-[4-(ethoxycarbonyl)methylpiperazin-1-yl]methyl}-[1,2,4]-thiadiazol-3-yl)-1-(tetrahydropyran-4-yl)methyl-1H-indole (1.26 g, 2.4 mmol; free base prepared according to the method of Example 2) was suspended in 4M aqueous sodium hydroxide (80 ml) and refluxed for 1 h. The reaction mixture was washed with diethyl ether (80 ml) and then acidified. The resulting precipitate was filtered off and dried, then triturated with methanol and filtered off to afford 3-[{5-[4-carboxymethylpiperazin-1-yl]methyl}-[1,2,4]-thiadiazol-3-yl]-7-chloro-1-(tetrahydropyran-4-yl)methyl-1H-indole as a white solid (1.20 g, 2.4 mmol). To a stirred solution of 3-[{5-[4-carboxymethylpiperazin-1-yl]methyl}-[1,2,4]-thiadiazol-3-yl]-7-chloro-1-(tetrahydropyran-4-yl)methyl-1H-indole (97 mg, 0.20 mmol) in dichloromethane (10 ml) was added N,N-diisopropylethylamine (240 µl, 1.39 mmol), ethylamine (2M solution in THF; 50 µl, 1.0 mmol) and 1-propylphosphonic acid cyclic anhydride (50% solution in ethyl acetate; 630 µl, 1.0 mmol). The reaction was stirred for 30 minutes, then diluted with ethyl acetate (30 ml) and washed with 5% aqueous sodium carbonate (2×20 ml), water (2×20 ml) and brine (2×20 ml). The organic layer was dried (MgSO$_4$), filtered and concentrated. The product was purified by HPLC [method (ii)] to afford the title compound as the free base (16 mg, 0.03 mmol). EsIMS: m/z 517.0 [M+H]$^+$.

EXAMPLE 4

7-Chloro-3-({5-[4-sulfamoylpiperazin-1-yl]methyl}-[1,2,4]-thiadiazol-3-yl)-1-(tetrahydropyran-4-yl)methyl-1H-indole, trifluoroacetic acid salt To a solution of piperazine (7.8 g, 90.7 mmol) and N,N-diisopropylethylamine (1.2 ml, 6.81 mmol) in 1-methyl-2-pyrrolidinone (10 ml) was slowly added methanesulfonic acid 3-(1-{tetrahydropyran-4-yl}methyl-7-chloro-1H-indol-3-yl)-[1,2,4]thiadiazol-5-ylmethyl ester (2 g, 4.54 mmol). The mixture was stirred at room temperature for 18 h, and then partitioned between water and diethyl ether. The organic layer was separated, dried (MgSO$_4$) and the solvent evaporated to afford crude 7-chloro-3-[{5-[piperazin-1-yl]methyl}-[1,2,4]-thiadiazol-3-yl]-1-(tetrahydropyran-4-yl)methyl-1H-indole (2.36 g).

A portion (100 mg) of this product was mixed with pyridine (2 ml) and sulfamide (89 mg, 0.93 mmol) and the mixture was subjected to microwave irradiation for 10 min at 180° C. The pyridine was evaporated off under reduced pressure and the residue partitioned between dichloromethane and 2M aqueous sodium hydroxide solution. The aqueous layer was extracted a further 2× with dichloromethane. The combined organic layers were dried over magnesium sulfate, filtered and concentrated under reduced pressure. The crude product was purified by HPLC [method (i)] to afford the title compound as a trifluoroacetic acid salt (47 mg, 0.08 mmol). EsIMS: m/z 511.0 [M+H]$^+$.

EXAMPLE 5

3-({5-[4-(Carbamoylmethyl)piperazin-1-yl]methyl}-[1,2,4]-thiadiazol-3-yl)-7-ethyl-1-(tetrahydropyran-4-yl)methyl-1H-indole, bis-hydrochloride salt The title compound was prepared following the method of Example 1, using 7-ethylindole instead of 7-chloroindole in step A. EsIMS: m/z 483.5 [M+H]$^+$.

EXAMPLE 6

A mixture of methanesulfonic acid 3-(1-{tetrahydropyran-4-yl}methyl-7-ethyl-1H-indol-3-yl)-[1,2,4]thiadiazol-5-ylmethyl ester (prepared according to the method of Example 1, step G, using 7-ethylindole instead of 7-chloroindole in step A; 50 mg, 0.11 mmol), potassium carbonate (15 mg, 0.11 mmol), the appropriate amine (0.17 mmol) and acetonitrile (1 ml) was subjected to microwave irradiation for 5 min at 150° C. The resulting mixtures were diluted with methanol, filtered and purified by HPLC [method (ii)] to afford the following compounds:

6a: 7-Ethyl-3-({5-[4-(2-hydroxyethyl)piperazin-1-yl]methyl}-[1,2,4]-thiadiazol-3-yl)-1-(tetrahydropyran-4-yl)methyl-1H-indole 1-(2-Hydroxyethyl)piperazine was used as the amine. Yield=33.9 mg (0.07 mmol). EsIMS: m/z 470.3 [M+H]$^+$.

6b: 7-Ethyl-3-({5-[4-(N-isopropylcarbamoyl)methylpiperazin-1-yl]methyl}-[1,2,4]-thiadiazol-3-yl)-1-(tetrahydropyran-4-yl)methyl-1H-indole N-Isopropyl-1-piperazineacetamide was used as the amine. Yield=31.1 mg (0.06 mmol). EsIMS: m/z 525.3 [M+H]$^+$.

6c: 7-Ethyl-3-({5-[3-ketopiperazin-1-yl]methyl}-[1,2,4]-thiadiazol-3-yl)-1-(tetrahydropyran-4-yl)methyl-1H-indole Piperazin-2-one was used as the amine. Yield=35.9 mg (0.08 mmol). EsIMS: m/z 440.0 [M+H]$^+$.

6d: 7-Ethyl-3-({5-[4-(methoxycarbonylmethyl)piperazin-1-yl]methyl}-[1,2,4]-thiadiazol-3-yl)-1-(tetrahydropyran-4-yl)methyl-1H-indole 1-(Methoxycarbonylmethyl)piperazine was used as the amine. Yield=7.7 mg (0.02 mmol). EsIMS: m/z 498.4 [M+H]$^+$.

EXAMPLE 7

A mixture of methanesulfonic acid 3-(1-{tetrahydropyran-4-yl}methyl-7-methoxy-1H-indol-3-yl)-[1,2,4]thiadiazol-5-ylmethyl ester (prepared according to the method of Example 1, step G, using 7-methoxyindole instead of 7-chloroindole in step A), potassium carbonate (1.5 equivalents), the appropriate amine (1.2 equivalents) and 1-methyl-2-pyrrolidinone was subjected to microwave irradiation for 5 min at 100° C. The reaction was worked up as described below.

7a: 3-({5-[4-(Carbamoylmethyl)piperazin-1-yl]methyl}-[1,2,4]-thiadiazol-3-yl)-7-methoxy-1-(tetrahydropyran-4-yl)methyl-1H-indole, bis-hydrochloride salt 2-piperazin-1-ylacetamide was used as the amine. Following microwave irradiation, the mixture was purified by flash column chromatography eluting with 0%-2% methanol in dichloromethane. The product was taken up in methanol and hydrogen chloride (excess; 2M solution in diethyl ether) was added. The mixture was concentrated in vacuo to afford the title compound. EsIMS: m/z 485.4 [M+H]$^+$.

7b: 3-({5-[4-(2-Hydroxyethyl)piperazin-1-yl]methyl}-[1,2,4]-thiadiazol-3-yl)-7-methoxy-1-(tetrahydropyran-4-yl)methyl-1H-indole, trifluoroacetic acid salt 1-(2-Hydroxyethyl)piperazine was used as the amine. Following microwave irradiation, the mixture was diluted with dichloromethane, filtered and purified by preparative LCMS to afford the title compound as a trifluoroacetic acid salt. EsIMS: m/z 472.1 [M+H]$^+$.

EXAMPLE 8

1-Cyclohexylmethyl-7-methoxy-3-({5-[4-(2-methoxyethyl)piperazin-1-yl]methyl}-[1,2,4]-thiadiazol-3-yl)-1H-indole, trifluoroacetic acid salt A mixture of methanesulfonic acid 3-(1-cyclohexylmethyl-7-methoxy-1H-indol-3-yl)-[1,2,4]thiadiazol-5-ylmethyl ester (prepared according to the method of Example 1, step G, using 7-methoxyindole instead of 7-chloroindole in step A and cyclohexylmethyl bromide instead of toluene-4-sulfonic acid tetrahydropyran-4-ylmethyl ester in step B; 100 mg, 0.23 mmol), 1-(2-methoxyethyl)-piperazine (174 µl, 1.15 mmol) and tetrahydrofuran (1 ml) was subjected to microwave irradiation for 15 minutes at 150° C. The resulting mixture was diluted with tetrahydrofuran (3 ml). Polymer supported isocyanate (Argonaut technologies, 1.25 mmol/g; 1.3 g) was added and the mixture was shaken for 2 hours followed by filtration, washing with dichloromethane. The filtrate was concentrated under reduced pressure and then purified by HPLC [method (i)] to afford the title compound as a trifluoroacetic acid salt (50 mg, 0.07 mmol). EsIMS: m/z 484.4 [M+H]$^+$.

EXAMPLE 9

3-({5-[4-(Carbamoylmethyl)piperazin-1-yl]methyl}-[1,2,4]-thiadiazol-3-yl)-7-chloro-1-(1,1-dioxo-hexahydrothiopyran-4-yl)methyl-1H-indole, bis-hydrochloride salt The title compound was prepared following the method of Example 1, using toluene-4-sulfonic acid 1,1-dioxo-hexahydro-1-thiopyran-4-ylmethyl ester instead of toluene-4-sulfonic acid tetrahydropyran-4-ylmethyl ester in step B. EsIMS: m/z 537.3 [M+H]$^+$.

EXAMPLE 10

3-({5-[3,5-Dimethylpiperazin-1-yl]methyl}-[1,2,4]-thiadiazol-3-yl)-6-fluoro-1-(tetrahydropyran-4-yl)methyl-1H-indole, trifluoroacetic acid salt A mixture of methanesulfonic acid 3-(1-{tetrahydropyran-4-yl}methyl-6-fluoro-1H-indol-3-yl)-[1,2,4]thiadiazol-5-ylmethyl ester (prepared according to the method of Example 1, step G, using 6-fluoroindole instead of 7-chloroindole in step A; 100 mg, 0.24 mmol), potassium carbonate (66 mg, 0.48 mmol), 2,6-dimethylpiperazine (32 mg, 0.28 mmol) and acetonitrile (3 ml) was subjected to microwave irradiation for 5 min at 150° C. The resulting mixture was diluted with methanol, filtered and purified by HPLC [method (i)] to afford the title compound as a trifluoroacetic acid salt (31 mg, 0.06 mmol). EsIMS: m/z 444.5 [M+H]$^+$.

EXAMPLE 11

3-({5-[4-(Carbamoylmethyl)piperazin-1-yl]methyl}-[1,2,4]-oxadiazol-3-yl)-7-chloro-1-(tetrahydropyran-4-yl)methyl-1H-indole, hydrochloride salt

Step A: 7-Chloro-1-(tetrahydropyran-4-yl)methyl-1H-indole-3-carbonitrile

Phosphorus oxychloride (9.6 ml, 103 mmol) was added dropwise, via a pressure equalising funnel, to a cooled (5-10° C.) solution of 7-chloro-1-(tetrahydropyran-4-yl)methyl-1H-indole-3-carboxylic acid amide (20.0 g, 68.3 mmol) in dimethylformamide (200 ml). Following complete addition of phosphorus oxychloride the reaction was left to stir for 10 mins before warming to room temperature and allowing to stir for a further 30 mins. The reaction mixture was then poured carefully into ice cold water (2000 ml), the resulting precipitate filtered off and washed with water. The filter cake was then dissolved in dichloromethane, washed with water and brine, dried over sodium sulfate and the solvent removed in vacuo. The resulting solid was crystallised from diethyl ether to yield 7-chloro-1-(tetrahydro-pyran-4-yl)methyl-1H-indole-3-carbonitrile (12.9 g, 46.9 mmol) as a white solid.

Step B: 7-Chloro-1-(tetrahydropyran-4-yl)methyl-1H-indole-3-carboxamidine

To a suspension of 7-chloro-1-(tetrahydropyran-4-yl)methyl-1H-indole-3-carbonitrile (12.9 g, 46.9 mmol) in ethanol (280 ml) and N,N-diisopropylethylamine (16.7 ml, 96.0 mmol) was added hydroxylamine hydrochloride (6.8 g, 121.4 mmol). The reaction mixture was warmed to reflux and stirred for 6 h before cooling to room temperature and the solvent removed in vacuo. The solid was dissolved in dichloromethane, washed with water and brine, dried over sodium sulfate and the solvent removed in vacuo. The resulting solid was crystallised from diethyl ether to yield 7-chloro-1-(tetrahydropyran-4-yl)methyl-1H-indole-3-carboxamidine (13.1 g, 42.5 mmol) as an off white solid.

Step C: 7-Chloro-3-[(5-chloromethyl)-([1,2,4]oxadiazol-3-yl)]-1-(tetrahydropyran-4-yl)methyl-1H-indole Molecular seives (5.3 g) were added to a stirred solution of 7-chloro-1-(tetrahydro-pyran-4-yl)methyl-1H-indole-3-carboxamidine (5.3 g, 17.2 mmol) in tetrahydrofuran (150 ml) and the reaction mixture was stirred for 60 mins. Sodium hydride (2.8 g, 116.6 mmol) was added portionwise and the reaction mixture allowed to stir for a further 60 mins before warming to 40° C. for 30 mins. The reaction was then cooled to −70° C. (dry ice/acetone bath) before the addition of chloroacetyl chloride (2.8 ml, 35.2 mmol) dropwise, via a pressure equalising funnel. The reaction was then allowed to warm to room temperature and stirred for a further 4 h before being quenched by the addition of water (5 ml), filtered and the solvent removed in vacuo. The solid was dissolved in dichloromethane, washed with water and brine, dried over sodium sulfate and the solvent removed in vacuo. The resulting residue was purified by flash column chromatography eluting with 1% (v/v) ethanol in dichloromethane through to 3% (v/v) ethanol in dichloromethane. The product containing fractions were combined, solvent removed in vacuo, and the resultant solid recrystallised from diethyl ether to yield 7-chloro-3-[(5-chloromethyl)-([1,2,4]oxadiazol-3-yl)]-1-(tetrahydro-pyran-4-yl)methyl-1H-indole (4.1 g, 11.2 mmol) as a white solid.

Step D: 3-({5-[4-(Carbamoylmethyl)piperazin-1-yl]methyl}-[1,2,4]-oxadiazol-3-yl)-7-chloro-1-(tetrahydropyran-4-yl)methyl-1H-indole, hydrochloride salt To a solution of 7-chloro-3-[(5-chloromethyl)-([1,2,4]-oxadiazol-3-yl)]-1-(tetrahydro-pyran-4-yl)methyl-1H-indole (50 mg, 0.14 mmol) in 1-methyl-2-pyrrolidinone (1 ml) was added 2-piperazin-1-ylacetamide (40 mg, 0.28 mmol) and potassium carbonate (28 mg, 0.20 mmol). The reaction was stirred at room temperature for 18 h. The reaction was diluted with dichloromethane (1 ml) and filtered through a 2 g Strata™ SCX giga tube. The tube was washed with methanol and then eluted with 2 M ammonia in methanol. The methanolic ammonia solution was evaporated and the residue purified by flash column chromatography, eluting with 0% to 8% (v/v) ethanol in dichloromethane. The purified product was dissolved in dichloromethane and hydrogen chloride (2M solution in diethyl ether; 0.2 ml, 0.4 mmol) was added. The hydrochloride salt was precipitated by addition of ethanol and diethyl ether and filtered off to afford the title compound (10 mg, 0.02 mmol). EsIMS: m/z 475.1, 473.1 [M+H]$^+$.

EXAMPLE 12

6-Bromo-3-({5-[4-(carbamoylmethyl)piperazin-1-yl]methyl}-[1,2,4]-oxadiazol-3-yl)-1-(tetrahydropyran-4-yl)methyl-1H-indole, hydrochloride salt 6-Bromo-1-(tetrahydropyran-4-yl)methyl-1H-indole-3-carboxylic acid amide was pre-pared following the method of Example 1, using 6-bromoindole instead of 7-chloroindole in step A. The title compound was prepared following the method of Example 11, using 6-bromo-1-(tetrahydropyran-4-yl)methyl-1H-indole-3-carboxylic acid amide instead of 7-chloro-1-(tetrahydropyran-4-yl)methyl-1H-indole-3-carboxylic acid amide in step A. EsIMS: m/z 519.3 [M+H]$^+$.

EXAMPLE 13

3-({5-[4-(Carbamoylmethyl)piperazin-1-yl]methyl}-[1,2,4]-oxadiazol-3-yl)-7-ethyl-1-(tetrahydropyran-4-yl)methyl-1H-indole 7-Ethyl-1-(tetrahydropyran-4-yl)methyl-1H-indole-3-carboxylic acid amide was prepared following the method of Example 1, using 7-ethylindole instead of 7-chloroindole in step A. The title compound was prepared following the method of Example 11, using 7-ethyl-1-(tetrahydropyran-4-yl)methyl-1H-indole-3-carboxylic acid amide instead of 7-chloro-1-(tetrahydropyran-4-yl)methyl-1H-indole-3-carboxylic acid amide in step A, and isolated as a free base following flash chromatography. EsIMS: m/z 467.3 [M+H]$^+$.

EXAMPLE 14

7-Chloro-3-({5-[4-(ethoxycarbonylmethyl)piperazin-1-yl]methyl}-[1,2,4]-oxadiazol-3-yl)-1-(1,1-dioxo-hexahydrothiopyran-4-yl)methyl-1H-indole 7-Choro-1-(1,1-dioxo-hexahydrothiopyran-4-yl)methyl-1H-indole-3-carboxylic acid amide was prepared following the method of Example 1, using toluene-4-sulfonic acid 1,1-dioxo-hexahydro-1-thiopyran-4-ylmethyl ester instead of toluene-4-sulfonic acid tetrahydro-pyran-4-ylmethyl ester in step B. 7-Chloro-3-[(5-chloromethyl)-([1,2,4]-oxadiazol-3-yl)]-1-(1,1-dioxo-hexahydrothiopyran-4-yl)methyl-1H-indole was prepared following the method of Example 11, using 7-choro-1-(1,1-dioxo-hexahydrothiopyran-4-yl)methyl-1H-indole-3-carboxylic acid amide instead of 7-chloro-1-(tetrahydropyran-4-yl)methyl-1H-indole-3-carboxylic acid amide in step A.

To a solution of 7-chloro-3-[(5-chloromethyl)-([1,2,4]-oxadiazol-3-yl)]-1-(1,1-dioxo-hexahydrothiopyran-4-yl)methyl-1H-indole (500 mg, 1.2 mmol) in 1-methyl-2-pyrrolidinone (10 ml) was added N,N-diisopropylethylamine (638 µl, 3.6 mmol) and 1-(ethoxycarbonyl-methyl)piperazine (417 mg, 2.4 mmol). The reaction was stirred at 50° C. for 18 h. The mixture was then partitioned between water (100 ml) and diethyl ether (100 ml). The layers were separated and the aqueous layer was extracted with diethyl ether (2×100 ml). The combined organic layers were washed with water (100 ml), brine (100 ml), dried (Na$_2$SO$_4$) and the solvent evaporated under reduced pressure. The residue was triturated with a dichloromethane/methanol/diethyl ether mixture to afford the title compound as a white solid (540 mg, 1.0 mmol). EsIMS: m/z 550.8 [M+H]$^+$.

EXAMPLE 15

7-Chloro-3-({5-[4-(methylcarbamoylmethyl)Piperazin-1-yl]methyl}-[1,2,4]-oxadiazol-3-yl)-1-(tetrahydropyran-4-yl)methyl-1H-indole, hydrochloride salt 7-Chloro-3-({5-[4-(ethoxycarbonyl)methylpiperazin-1-yl]methyl}-[1,2,4]-oxadiazol-3-yl)-1-(tetrahydropyran-4-yl)methyl-1H-indole was prepared according to the method of Example 14, using 7-chloro-3-[(5-chloromethyl)-([1,2,4]oxadiazol-3-yl)]-1-(tetrahydropyran-4-yl)methyl-1H-indole instead of 7-chloro-3-[(5-chloromethyl)-([1,2,4]oxadiazol-3-yl)]-1-(1,1-dioxo-hexahydrothiopyran-4-yl)methyl-1H-indole.

7-chloro-3-({5-[4-(ethoxycarbonyl)methylpiperazin-1-yl]methyl}-[1,2,4]-oxadiazol-3-yl)-1-(tetrahydropyran-4-yl)methyl-1H-indole (660 mg, 1.3 mmol) was suspended in 2M aqueous sodium hydroxide solution (30 ml) and the mixture was heated to reflux for 1 h. The reaction mixture was washed with diethyl ether (30 ml) and then acidified. The resulting precipitate was filtered off and dried, then triturated with a mixture of dichloromethane, methanol and diethyl ether to afford 3-({5-[4-carboxymethylpiperazin-1-yl]methyl}-[1,2,4]-oxadiazol-3-yl)-7-chloro-1-(tetrahydropyran-4-yl)methyl-1H-indole as an off-white solid (537 mg, 1.1 mmol). To a stirred solution of 3-({5-[4-carboxymethylpiperazin-1-yl]methyl}-[1,2,4]-oxadiazol-3-yl)-7-chloro-1-(tetrahydropyran-4-yl)methyl-1H-indole (50 mg, 0.11 mmol) in dichloromethane (1 ml) was added N,N-diisopropylethylamine (130 µl, 0.74 mmol), methylamine (2M solution in THF; 550 µl, 1.1 mmol) and 1-propylphosphonic acid cyclic anhydride (50% solution in ethyl acetate; 705 µl, 1.1 mmol). The reaction was stirred for 4 h, then diluted with ethyl acetate (10 ml) and washed with 5% aqueous sodium carbonate (3×15 ml), water (3×15 ml) and brine (2×15 ml). The organic layer was dried (MgSO$_4$), filtered and concentrated. The resulting gum was dissolved in dichloromethane and methanol and hydrogen chloride (2M solution in diethyl ether; 0.2 ml, 0.4 mmol) was added. The hydrochloride salt was precipitated by addition of diethyl ether and filtered off to afford the title compound (13.6 mg, 0.03 mmol). EsIMS: m/z 487.5 [M+H]+.

EXAMPLE 16

The following compounds were prepared according to the method of Example 15, using alternative amines instead of methylamine 16a: 7-Chloro-3-({5-[4-(methoxyethylcarbamoylmethyl)piperazin-1-yl]methyl}-[1,2,4]-oxadiazol-3-yl)-1-(tetrahydropyran-4-yl)methyl-1H-indole, hydrochloride salt 2-Methoxyethylamine was used as the amine. EsIMS: m/z 531.2 [M+H]+.

16b: 7-Chloro-3-({5-[4-(hydroxyethylcarbamoylmethyl)piperazin-1-yl]methyl}-[1,2,4]-oxadiazol-3-yl)-1-(tetrahydropyran-4-yl)methyl-1H-indole, hydrochloride salt 2-Hydroxyethylamine was used as the amine. EsIMS: m/z 517.2 [M+H]+.

16c: 7-Chloro-3-({5-[4-(cyclopropylmethylcarbamoylmethyl)piperazin-1-yl]methyl}-[1,2,4]-oxadiazol-3-yl)-1-(tetrahydropyran-4-yl)methyl-1H-indole, hydrochloride salt Cyclopropylmethylamine was used as the amine. EsIMS: m/z 527.3 [M+H]+.

EXAMPLE 17

7-Chloro-3-({5-[4-([1,2,4]oxadiazol-3-ylmethyl)piperazin-1-yl]methyl}-[1,2,4]-oxadiazol-3-yl)-1-(1,1-dioxo-hexahydrothiopyran-4-yl)methyl-1H-indole To a solution of 7-chloro-3-[(5-chloromethyl)-([1,2,4]oxadiazol-3-yl)]-1-(1,1-dioxo-hexahydrothiopyran-4-yl)methyl-1H-indole (500 mg, 1.2 mmol) in 1-methyl-2-pyrrolidinone (15 ml) was added N,N-diisopropylethylamine (480 µl, 2.7 mmol) and piperazine (470 mg, 5.4 mmol). The reaction was stirred at room temperature for 18 h. The mixture was then partitioned between water (100 ml) and diethyl ether (100 ml). The layers were separated and the aqueous layer was extracted with diethyl ether (2×100 ml). The combined organic layers were washed with water (100 ml), brine (100 ml), dried (Na$_2$SO$_4$) and the solvent evaporated under reduced pressure to afford 7-chloro-3-({5-[piperazin-1-yl]methyl}-[1,2,4]-oxadiazol-3-yl)-1-(1,1-dioxo-hexahydrothiopyran-4-yl)methyl-1H-indole (400 mg, 0.96 mmol). To a solution of 7-chloro-3-({5-[piperazin-1-yl]methyl}-[1,2,4]-oxadiazol-3-yl)-1-(1,1-dioxo-hexahydrothiopyran-4-yl)methyl-1H-indole (50 mg, 0.11 mmol) in dichloromethane (2 ml) and N,N-diisopropylethylamine (38 µl, 0.22 mmol) was added 3-(chloromethyl)-[1,2,4]oxadiazole (19 mg, 0.16 mmol). The reaction was stirred at room temperature for 18 h. The reaction was filtered through a 2 g Strata™ SCX giga tube, washing with dichloromethane, methanol and then eluting with 2 M ammonia in methanol. The methanolic ammonia solution was evaporated under reduced pressure and the residue purified by flash column chromatography, eluting with 0% to 8% ethanol in dichloromethane to afford the title compound (49 mg, 0.09 mmol). EsIMS: m/z 546.3 [M+H]+.

EXAMPLE 18

3-[5-[4-(tert-Butoxycarbonyl)-cis-2,6-dimethylpiperazin-1-ylmethyl]-[1,2,4]-oxadiazol-3-yl]-7-chloro-1-[(tetrahydropyran-4-yl)methyl]-1H-indole A mixture of 7-chloro-3-[(5-chloromethyl)-([1,2,4]-oxadiazol-3-yl)]-1-(tetrahydropyran-4-yl)methyl-1H-indole (73 mg, 0.20 mmol), 4-Boc-cis-2,6-dimethylpiperazine (64 mg, 0.30 mmol), N,N-diisopropylethylamine (78 mg, 0.60 mmol) and sodium iodide (30 mg, 0.20 mmol) in dimethylformamide (2.0 ml) was subjected to microwave irradiation at 160° C. for 5 minutes, then filtered through a 5 g Strata™ SCX giga tube, eluting with dichloromethane, methanol and then 2 M ammonia in methanol. The product was purified by flash chromatography eluting with 50% (v/v) ethyl acetate in heptane then ethyl acetate to afford the title compound (40.2 mg, 0.074 mmol). EsIMS: m/z 566.5, 544.7 [M+H]+, 488.3, 444.5.

EXAMPLE 19

7-Chloro-3-[5-(cis-2,6-dimethylpiperazin-1-ylmethyl)-[1,2,4]-oxadiazol-3-yl]-1-[(tetrahydropyran-4-yl)methyl]-1H-indole, trifluoroacetic acid salt A mixture of 3-[5-[4-(tert-butoxycarbonyl)-cis-2,6-dimethylpiperazin-1-ylmethyl]-[1,2,4]-oxadiazol-3-yl]-7-chloro-1-[(tetrahydropyran-4-yl)methyl]-1H-indole (38 mg, 0.070 mmol) and 5N hydrochloric acid (0.2 ml) in 1,4-dioxane (2.0 ml) was stirred at room temperature for 1 h, then at 90° C. for 0.5 h. The mixture was filtered through a 5 g Strata™ SCX giga tube, eluting with dichloromethane, methanol and then 2 M ammonia in methanol, and purified by HPLC [method (i)] to afford the title compound as a trifluoroacetic acid salt (14.4 mg, 0.026 mmol). EsIMS: m/z 444.6 [M+H]+, 418.8, 386.9.

EXAMPLE 20

3-[5-[4-(Carbamoylmethyl)-cis-2,6-dimethylpiperazin-1-ylmethyl]-[1,2,4]-oxadiazol-3-yl]-7-chloro-1-[(tetrahydropyran-4-yl)methyl]-1H-indole, trifluoroacetic acid salt A mixture of 7-chloro-3-[5-(cis-2,6-dimethylpiperazin-1-ylmethyl)-[1,2,4]-oxadiazol-3-yl]-1-[(tetrahydropyran-4-yl)methyl]-1H-indole (10 mg, 0.023 mmol), 2-bromoacetamide (4.7 mg, 0.034 mmol), N,N-diisopropylethylamine (4.4 mg, 0.034 mmol) and sodium iodide (1.0 mg, 0.007 mmol) in acetonitrile (2.0 ml) was subjected to microwave irradiation at 100° C. for 5 minutes. The mixture was filtered through a 5 g Strata™ SCX giga tube, eluting with dichloromethane, methanol and then 2 M ammonia in methanol, and purified by HPLC [method (i)] to afford the title compound as a trifluoroacetic acid salt (12.2 mg, 0.020 mmol). EsIMS: m/z 501.4 [M+H]+, 432.8, 387.1.

EXAMPLE 21

The method of Examples 18 to 20 was further used to prepare the following compounds.

21a: (R)-3-{5-[4-(Carbamoylmethyl)-2-methylpiperazin-1-ylmethyl]-[1,2,4]-oxadiazol-3-yl}-7-chloro-1-[(tetrahydropyran-4-yl)methyl]-1H-indole, trifluoroacetic acid salt (R)-4-Boc-2-methylpiperazine was used instead of 4-Boc-cis-2,6-dimethylpiperazine EsIMS: m/z 509.3, 487.5 [M+H]+, 473.5.

21b: (S)-3-{5-[4-(Carbamoylmethyl)-2-methylpiperazin-1-ylmethyl]-[1,2,4]-oxadiazol-3-yl}-7-chloro-1-[(tetrahydropyran-4-yl)methyl]-1H-indole, trifluoroacetic acid salt (S)-4-Boc-2-methylpiperazine was used instead of 4-Boc-cis-2,6-dimethylpiperazine. EsIMS: m/z 509.3, 487.5 [M+H]$^+$, 170.1.

21c: 3-{5-[4-(Carbamoylmethyl)-2-hydroxymethylpiperazin-1-ylmethyl]-[1,2,4]-oxadiazol-3-yl}-7-chloro-1-[(tetrahydropyran-4-yl)methyl]-1H-indole, trifluoroacetic acid salt 4-Boc-2-hydroxymethylpiperazine was used instead of 4-Boc-cis-2,6-dimethylpiperazine. EsIMS: m/z 525.5, 503.0 [M+H]$^+$, 485.9.

21d: 3-{5-[4-(Carbamoylmethyl)-homopiperazin-1-ylmethyl]-[1,2,4]-oxadiazol-3-yl}-7-chloro-1-[(tetrahydropyran-4-yl)methyl]-1H-indole, trifluoroacetic acid salt 1-Boc-homopiperazine was used instead of 4-Boc-cis-2,6-dimethylpiperazine. EsIMS: m/z 509.3, 487.5 [M+H]$^+$, 387.4, 170.1.

21e: (1S,4S)-3-[5-[5-(Carbamoylmethyl)-2,5-diazabicyclo[2.2.1]heptan-2-ylmethyl]-[1,2,4]-oxadiazol-3-yl]-7-chloro-1-[(tetrahydropyran-4-yl)methyl]-1H-indole, trifluoroacetic acid salt (1S,4S)-2-Boc-2,5-diazabicyclo[2.2.1]heptane was used instead of 4-Boc-cis-2,6-dimethylpiperazine. EsIMS: m/z 507.3, 485.8 [M+H]$^+$, 168.6.

EXAMPLE 22

(R)-7-Chloro-3-[5-(3-methylpiperazin-1-ylmethyl)-[1,2,4]-oxadiazol-3-yl]-1-[(tetrahydropyran-4-yl)methyl]-1H-indole, trifluoroacetic acid salt A mixture of 7-chloro-3-[(5-chloromethyl)-([1,2,4]-oxadiazol-3-yl)]-1-(tetrahydropyran-4-yl)methyl-1H-indole (73 mg, 0.20 mmol), (R)-2-methylpiperazine (30 mg, 0.30 mmol), N,N-diisopropylethylamine (78 mg, 0.60 mmol) and sodium iodide (30 mg, 0.20 mmol) in acetonitrile (1.0 ml) and dimethylformamide (1.0 ml) was subjected to microwave irradiation at 160° C. for 5 minutes. The mixture was filtered through a 5 g Strata™ SCX giga tube, eluting with dichloromethane, methanol and then 2 M ammonia in methanol, and purified by HPLC [method (i)] to afford the title compound as a trifluoroacetic acid salt (73 mg, 0.13 mmol). EsIMS: m/z 430.1 [M+H]$^+$, 113.2.

EXAMPLE 23

(S)-7-Chloro-3-[5-(3-hydroxymethylpiperazin-1-ylmethyl)-[1,2,4]-oxadiazol-3-yl]-1-[(tetrahydropyran-4-yl)methyl]-1H-indole trifluoroacetic acid salt The title compound was synthesised according to the method of Example 22, using (S)-2-hydroxymethylpiperazine instead of (R)-2-methylpiperazine. EsIMS: m/z 446.3 [M+H]$^+$, 428.6.

EXAMPLE 24

(S)-7-Chloro-3-[5-[3-hydroxymethyl-4-(methylcarbamoylmethyl)piperazin-1-ylmethyl]-[1,2,4]-oxadiazol-3-yl]-1-[(tetrahydropyran-4-yl)methyl]-1H-indole A mixture of (S)-7-chloro-3-[5-(3-hydroxymethylpiperazin-1-ylmethyl)-[1,2,4]-oxadiazol-3-yl]-1-[(tetrahydropyran-4-yl)methyl]-1H-indole (22 mg, 0.049 mmol), N-methyl-2-chloroacetamide (11 mg, 0.098 mmol), N,N-diisopropylethylamine (19 mg, 0.15 mmol) and sodium iodide (7 mg, 0.049 mmol) in dimethylformamide (2.0 ml) was subjected to microwave irradiation at 160° C. for 5 minutes. The mixture was filtered through a 5 g Strata™ SCX giga tube, eluting with dichloromethane, methanol and then 2 M ammonia in methanol, and purified by flash column chromatography eluting with ethyl acetate to 33% (v/v) methanol in ethyl acetate to afford the title compound (23.9 mg, 0.046 mmol). EsIMS: m/z 539.8, 517.5 [M+H]$^+$, 503.1, 200.6.

EXAMPLE 25

The method of Examples 22 to 24 was further used to prepare the following compounds.

25a: (R)-7-Chloro-3-[5-[3-hydroxymethyl-4-(methylcarbamoylmethyl)piperazin-1-ylmethyl]-[1,2,4]-oxadiazol-3-yl]-1-[(tetrahydropyran-4-yl)methyl]-1H-indole EsIMS: m/z 539.7, 517.7 [M+H]$^+$, 503.4, 200.1.

25b: (S)-7-Chloro-3-[5-[4-(dimethylcarbamoylmethyl)-3-hydroxymethylpiperazin-1-ylmethyl]-[1,2,4]-oxadiazol-3-yl]-1-[(tetrahydropyran-4-yl)methyl]-1H-indole EsIMS: m/z 553.7, 531.2 [M+H]$^+$, 214.3.

25c: (R)-7-Chloro-3-[5-[4-(dimethylcarbamoylmethyl)-3-hydroxymethylpiperazin-1-ylmethyl]-[1,2,4]-oxadiazol-3-yl]-1-[(tetrahydropyran-4-yl)methyl]-1H-indole EsIMS: m/z 553.3, 531.2 [M+H]$^+$, 214.4.

25d: 3-[5-[4-(Carbamoylmethyl)-3-methoxycarbonylpiperazin-1-ylmethyl]-[1,2,4]-oxadiazol-3-yl]-7-chloro-1-[(tetrahydropyran-4-yl)methyl]-1H-indole EsIMS: m/z 553.5, 531.2 [M+H]$^+$, 488.5, 214.4.

EXAMPLE 26

7-Chloro-3-[5-(trans-2,5-dimethylpiperazin-1-ylmethyl)-[1,2,4]-oxadiazol-3-yl]-1-[(tetrahydropyran-4-yl)methyl]-1H-indole trifluoroacetic acid salt A mixture of 7-chloro-3-[(5-chloromethyl)-([1,2,4]-oxadiazol-3-yl)]-1-(tetrahydropyran-4-yl)methyl-1H-indole (73 mg, 0.20 mmol), trans-2,5-dimethylpiperazine (69 mg, 0.60 mmol), N,N-diisopropylethylamine (78 mg, 0.60 mmol) and sodium iodide (30 mg, 0.20 mmol) in dimethylformamide (2.0 ml) was subjected to microwave irradiation at 160° C. for 5 minutes. The mixture was filtered through a 5 g Strata™ SCX giga tube, eluting with dichloromethane, methanol and then 2 M ammonia in methanol then purified by HPLC [method (i)] to afford the title compound as a trifluoroacetic acid salt (6.7 mg, 0.012 mmol). EsIMS: m/z 444.5 [M+H]$^+$, 126.4.

EXAMPLE 27

3-[5-[4-(Carbamoylmethyl)-trans-2,5-dimethylpiperazin-1-ylmethyl]-[1,2,4]-oxadiazol-3-yl]-7-chloro-1-[(tetrahydropyran-4-yl)methyl]-1H-indole trifluoroacetic acid salt A mixture of 7-chloro-3-[5-(trans-2,5-dimethylpiperazin-1-ylmethyl)-[1,2,4]-oxadiazol-3-yl]-1-[(tetrahydropyran-4-yl)methyl]-1H-indole (10 mg, 0.023 mmol), 2-bromoacetamide (4.7 mg, 0.034 mmol), N,N-diisopropylethylamine (4.4 mg, 0.034 mmol) and sodium iodide (1.0 mg, 0.007 mmol) in dimethylformamide (2.0 ml) was subjected to microwave irradiation at 160° C. for 5 minutes. The mixture was filtered through a 5 g Strata™ SCX giga tube, eluting with dichloromethane, methanol and then 2 M ammonia in methanol then purified by HPLC [method (i)] to afford the title compound as a trifluoroacetic acid salt (11.3 mg, 0.018 mmol). EsIMS: m/z 523.5, 501.4 [M+H]$^+$, 184.3.

EXAMPLE 28

3-[5-[4-(Carbamoylmethyl)-cis-3,5-dimethylpiperazin-1-ylmethyl]-[1,2,4]-oxadiazol-3-yl]-7-chloro-1-[(tetrahydropyran-4-yl)methyl]-1H-indole trifluoroacetic acid salt A mixture of 7-chloro-3-[(5-chloromethyl)-([1,2,4]-oxadiazol-3-yl)]-1-(tetrahydropyran-4-yl)methyl-1H-indole (73 mg, 0.20 mmol), cis-2,6-dimethylpiperazine (69 mg, 0.60 mmol), N,N-diisopropylethylamine (78 mg, 0.60 mmol) and sodium iodide (30 mg, 0.20 mmol) in dimethylformamide (2.0 ml) was subjected to microwave irradiation at 160° C. for 5 minutes. The mixture was filtered through a 5 g Strata™ SCX giga tube, eluting with dichloromethane, methanol and then 2 M ammonia in methanol to afford crude 7-chloro-3-[5-[cis-3,5-dimethylpiperazin-1-ylmethyl]-[1,2,4]-oxadiazol-3-yl]-1-[(tetrahydropyran-4-yl)methyl]-1H-indole, 10 mg (0.023 mmol) of which was mixed with 2-bromoacetamide (4.7 mg, 0.034 mmol), N,N-diisopropylethylamine (4.4 mg, 0.034 mmol) and sodium iodide (1.0 mg, 0.007 mmol) in acetonitrile (2.0 ml). The mixture was subjected to microwave irradiation at 160° C. for 5 minutes. The mixture was filtered through a 5 g Strata™ SCX giga tube, eluting with dichloromethane, methanol and then 2 M ammonia in methanol and purified by HPLC [method (i)] to afford a mixture of 3-[5-[4-(carbamoylmethyl)-cis-3,5-dimethylpiperazin-1-ylmethyl]-[1,2,4]-oxadiazol-3-yl]-7-chloro-1-[(tetrahydropyran-4-yl)methyl]-1H-indole trifluoro-acetic acid salt and the trifluoroacetic acid salt of the starting material (7-chloro-3-[5-[cis-3,5-dimethylpiperazin-1-ylmethyl]-[1,2,4]-oxadiazol-3-yl]-1-[(tetrahydropyran-4-yl)methyl]-1H-indole). To remove the starting material as the corresponding acetamide derivative, the mixture (5.5 mg) was reacted with acetyl chloride (4.0 mg, 0.05 mmol) in the presence of N,N-diisopropylethylamine (6.5 mg, 0.05 mmol) in dichloromethane (1.0 ml) at room temperature for 0.5 h and the reaction mixture was quenched with methanol (0.2 ml), then filtered through a 5 g Strata™ SCX giga tube, eluting with dichloromethane, methanol and then 2 M ammonia in methanol and purified by HPLC [method (i)] to afford the title compound as a trifluoroacetic acid salt (5.1 mg, 0.008 mmol). EsIMS: m/z 523.8, 501.5 [M+H]$^+$, 184.1.

EXAMPLE 29

(R)-3-[5-[4-(Carbamoylmethyl)-3-methylpiperazin-1-ylmethyl]-[1,2,4]-oxadiazol-3-yl]-7-chloro-1-[(tetrahydropyran-4-yl)methyl]-1H-indole trifluoroacetic acid salt A mixture of (R)-1-Boc-3-methylpiperazine (100 mg, 0.50 mmol), 2-bromoacetamide (103 mg, 0.75 mmol), N,N-diisopropylethylamine (129 mg, 1.00 mmol) and sodium iodide (7.5 mg, 0.050 mmol) in acetonitrile (2.0 ml) was subjected to microwave irradiation at 100° C. for 5 minutes. The mixture was filtered through a 5 g Strata™ SCX giga tube, eluting with dichloromethane, methanol and then 2 M ammonia in methanol, and purified by flash chromatography eluting with ethyl acetate to 17% (v/v) methanol in ethyl acetate to afford (R)-2-(4-Boc-2-methylpiperazin-1-yl)acetamide (114 mg, 0.44 mmol).

A mixture of (R)-2-(4-Boc-2-methylpiperazin-1-yl)acetamide (114 mg, 0.44 mmol) and 5N hydrochloric acid (0.2 ml) in 1,4-dioxane (2.0 ml) was stirred at 90° C. for 20 min. The mixture was concentrated in vacuo to afford (R)-2-(2-methylpiperazin-1-yl)acetamide hydrochloride salt quantitatively.

A mixture of 7-chloro-3-[(5-chloromethyl)-([1,2,4]-oxadiazol-3-yl)]-1-(tetrahydropyran-4-yl)-methyl-1H-indole (73 mg, 0.20 mmol), (R)-2-(2-methylpiperazin-1-yl)acetamide hydrochloride salt (101 mg, 0.44 mmol), N,N-diisopropylethylamine (129 mg, 1.00 mmol) and sodium iodide (30 mg, 0.20 mmol) in dimethylformamide (2.0 ml) was subjected to microwave irradiation at 160° C. for 5 minutes, then filtered through a 5 g Strata™ SCX giga tube, eluting with dichloromethane, methanol and then 2 M ammonia in methanol, and purified by HPLC [method (i)] to afford the title compound as a trifluoroacetic acid salt (89.1 mg, 0.148 mmol). EsIMS: m/z 509.5, 487.5 [M+H]$^+$, 170.4.

EXAMPLE 30

(S)-3-[5-[4-(Carbamoylmethyl)-3-methylpiperazin-1-ylmethyl]-[1,2,4]-oxadiazol-3-yl]-7-chloro-1-[(tetrahydropyran-4-yl)methyl]-1H-indole trifluoroacetic acid salt The title compound was prepared according to the method of Example 29, using (S)-1-Boc-3-methylpiperazine instead of (R)-1-Boc-3-methylpiperazine. EsIMS: m/z 509.6, 487.5 [M+H]$^+$, 170.3.

EXAMPLE 31

3-({4-[4-(Carbamoylmethyl)piperazin-1-yl]methyl}-[1,3]-thiazol-2-yl)-7-chloro-1-(tetrahydropyran-4-yl)methyl-1H-indole A mixture of 7-chloro-1-(tetrahydropyran-4-yl)methyl-1H-indole-3-carboxylic acid amide (1.8 g, 6.0 mmol), Lawesson's reagent (4.85 g, 12.0 mmol), toluene (150 ml) and tetrahydrofuran (50 ml) was stirred at room temperature for 3 days. The reaction mixture was concentrated in vacuo and the obtained reside was purified by column chromatography eluting with 20-50% (v/v) ethyl acetate in n-heptane to afford 7-chloro-1-(tetrahydropyran-4-yl)methyl-1H-indole-3-carbothioic acid amide (1.4 g, 4.5 mmol).

A mixture of 7-chloro-1-(tetrahydropyran-4-yl)methyl-1H-indole-3-carbothioic acid amide (920 mg, 3.0 mmol), 1,3-dichloroacetone (571 mg, 4.50 mmol) in toluene (30 ml) was stirred at 40° C. for 18 h. The reaction mixture was concentrated in vacuo, and the obtained crystals were washed with 10% dichloromethane (v/v) in n-heptane to give 7-chloro-3-[4-(chloromethyl)-[1,3]-thiazol-2-yl]-1-(tetrahydropyran-4-yl)methyl-1H-indole (590 mg, 1.5 mmol).

A mixture of 7-chloro-3-[4-(chloromethyl)-[1,3]-thiazol-2-yl]-1-(tetrahydropyran-4-yl)methyl-1H-indole (40 mg, 0.11 mmol), 2-piperazin-1-ylacetamide (32 mg, 0.15 mmol), N,N-diisopropylethylamine (27 mg, 0.21 mmol), sodium iodide (16 mg, 0.11 mmol) and dimethylformamide (2 ml) was subjected to microwave irradiation for 5 min at 160° C. The reaction mixture was filtered through a 5 g Strata™ SCX giga tube. The tube was washed with methanol and then eluted with 2 M ammonia in methanol. The methanolic ammonia solution was concentrated in vacuo and the obtained residue was purified by column chromatography eluting with 0-3% (v/v) (2 M ammonia in methanol) in dichloromethane to afford the title compound (30.6 mg, 0.06 mmol). EsIMS: m/z 490.4, 488.5 [M+H]$^+$.

EXAMPLE 32

In-Vitro Determination of Efficacy and Potency at the Human CB1 Receptor Expressed in CHO Cells Chinese Hamster Ovary (CHO) cells expressing the human CB1 receptor and a luciferase reporter gene were suspended in phenol red/serum free DMEM/F-12 nut mix containing penicillin/streptomycin (50 U/50 µg/ml) and fungizone (1 µg/ml) and seeded into 96 well plates at a density of 3×10$^4$ cells per well (100 µl final volume). Cells were incubated overnight (approx. 18 h at 37° C., 5% $CO_2$/95% air) prior to assay.

The test compound (10 mM solution in dimethylsulfoxide) was diluted in F12 Nut Mix to give a range of stock solutions from 0.11 mM to 0.11 nM. The stock solutions (10 µl) were added directly to the relevant wells. The plates were incubated at 37° C. for 5 h to allow agonist-induced expression of the luciferase enzyme. Under subdued light, LucLite substrate (Packard; reconstituted as per manufacturer's instructions; 100 µl) was added to each well. Plates were covered with Top Seal and then incubated at room temperature for 5 minutes before counting on the Packard TopCount (single photon counting, 0.01 minute count time, 5 minute count delay).

A "best-fit" curve was fitted by a minimum sum of squares method to the plot of counts per second (CPS) against compound concentration (M) to obtain an $EC_{50}$ value. Table 1 shows the $pEC_{50}$ values obtained for some representative compounds of the invention.

TABLE 1

| Example | Chemical name | Chemical structure | $pEC_{50}$ |
|---|---|---|---|
| 1 | 3-({5-[4-(Carbamoylmethyl)piperazin-1-yl]methyl}-[1,2,4]-thiadiazol-3-yl)-7-chloro-1-(tetrahydropyran-4-yl)methyl-1H-indole, bis-hydrochloride salt | 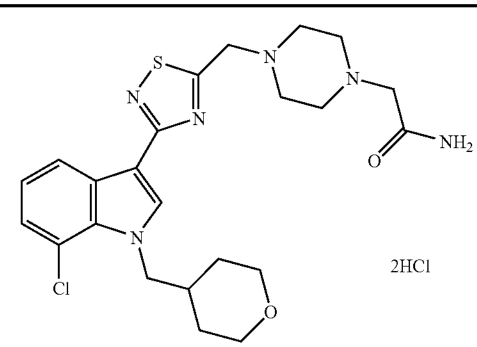 | 7.8 |
| 3 | 7-Chloro-3-({5-[4-(ethylcarbamoylmethyl)piperazin-1-yl]methyl}-[1,2,4]-thiadiazol-3-yl)-1-(tetrahydropyran-4-yl)methyl-1H-indole | 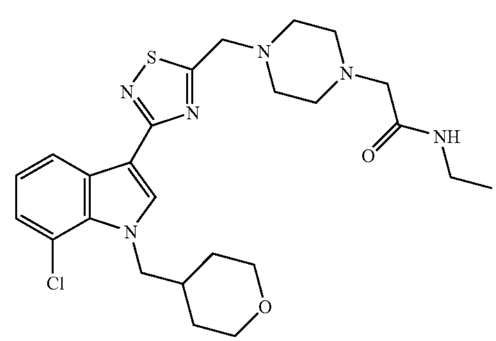 | 7.4 |

TABLE 1-continued

| Example | Chemical name | Chemical structure | pEC$_{50}$ |
|---|---|---|---|
| 4 | 7-Chloro-3-({5-[4-sulfamoylpiperazin-1-yl]methyl}-[1,2,4]-thiadiazol-3-yl)-1-(tetrahydropyran-4-yl)methyl-1H-indole, trifluoroacetic acid salt | 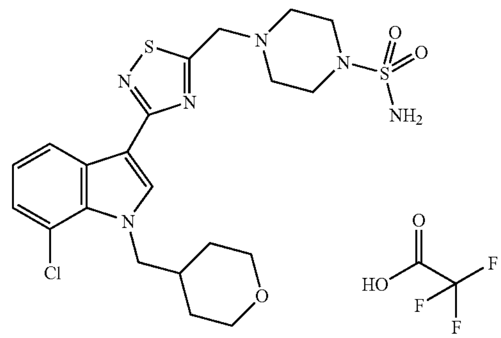 | 6.7 |
| 6b | 7-Ethyl-3-({5-[4-(N-isopropylcarbamoyl)methylpiperazin-1-yl]methyl}-[1,2,4]-thiadiazol-3-yl)-1-(tetrahydropyran-4-yl)methyl-1H-indole | 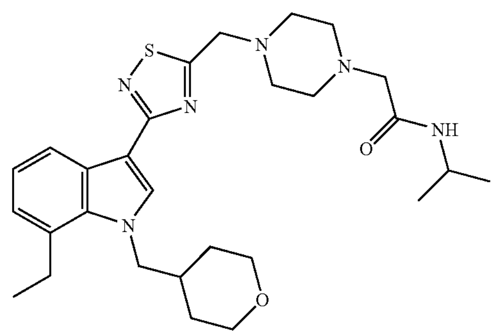 | 7.3 |
| 6d | 7-Ethyl-3-({5-[4-(methoxycarbonylmethyl)piperazin-1-yl]methyl}-[1,2,4]-thiadiazol-3-yl)-1-(tetrahydropyran-4-yl)methyl-1H-indole | 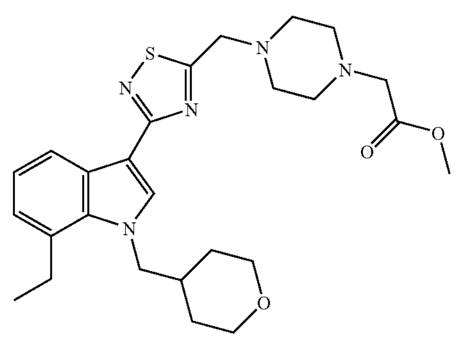 | 7.2 |
| 7a | 3-({5-[4-(Carbamoylmethyl)piperazin-1-yl]methyl}-[1,2,4]-thiadiazol-3-yl)-7-methoxy-1-(tetrahydropyran-4-yl)-methyl-1H-indole, bis-hydrochloride salt | 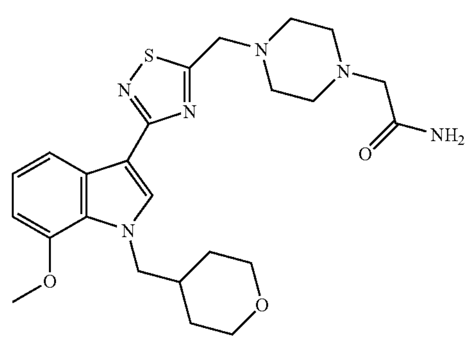 | 7.0 |

TABLE 1-continued

| Example | Chemical name | Chemical structure | pEC$_{50}$ |
| --- | --- | --- | --- |
| 9 | 3-({5-[4-(Carbamoylmethyl)piperazin-1-yl]methyl}-[1,2,4]-thiadiazol-3-yl)-7-chloro-1-(1,1-dioxo-hexahydrothiopyran-4-yl)methyl-1H-indole, bis-hydrochloride salt | 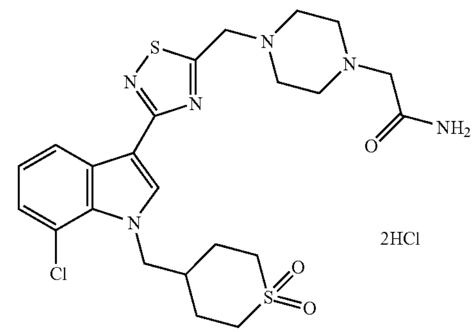 | 6.7 |
| 11 | 3-({5-[4-(Carbamoylmethyl)piperazin-1-yl]methyl}-[1,2,4]-oxadiazol-3-yl)-7-chloro-1-(tetrahydropyran-4-yl)methyl-1H-indole, hydrochloride salt | 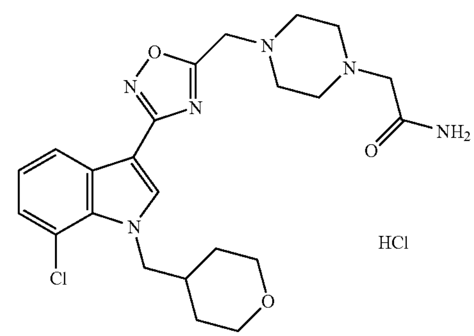 | 7.1 |
| 17 | 7-Chloro-3-({5-[4-([1,2,4]-oxadiazol-3-ylmethyl)piperazin-1-yl]methyl}-[1,2,4]-oxadiazol-3-yl)-1-(1,1-dioxo-hexahydrothiopyran-4-yl)methyl-1H-indole | 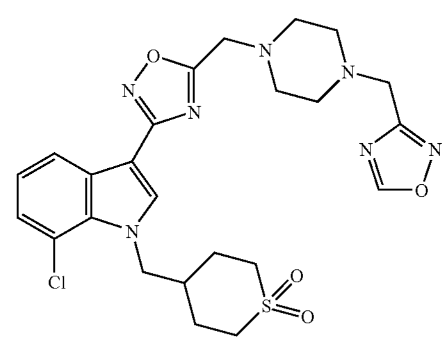 | 6.8 |
| 18 | 3-[5-[4-(tert-Butoxycarbonyl)-cis-2,6-dimethylpiperazin-1-ylmethyl]-[1,2,4]-oxadiazol-3-yl]-7-chloro-1-[(tetrahydropyran-4-yl)methyl]-1H-indole | 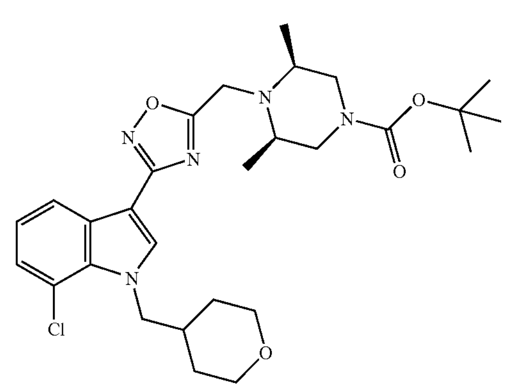 | 6.7 |

TABLE 1-continued

| Example | Chemical name | Chemical structure | pEC$_{50}$ |
|---|---|---|---|
| 21d | 3-{5-[4-(Carbamoylmethyl)-homopiperazin-1-ylmethyl]-[1,2,4]-oxadiazol-3-yl}-7-chloro-1-[(tetrahydropyran-4-yl)methyl]-1H-indole, trifluoroacetic acid salt | 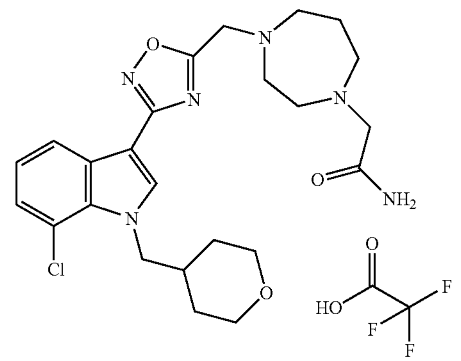 | 7.2 |
| 24 | (S)-7-Chloro-3-[5-[3-hydroxymethyl-4-(methylcarbamoylmethyl)piperazin-1-ylmethyl]-[1,2,4]-oxadiazol-3-yl]-1-[(tetrahydropyran-4-yl)methyl]-1H-indole | 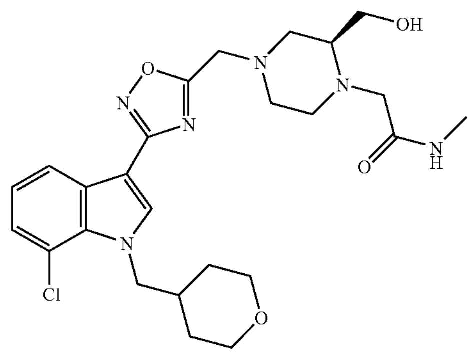 | 7.9 |
| 31 | 3-({4-[4-(Carbamoylmethyl)piperazin-1-yl]methyl}-[1,3]-thiazol-2-yl)-7-chloro-1-(tetrahydropyran-4-yl)methyl-1H-indole | 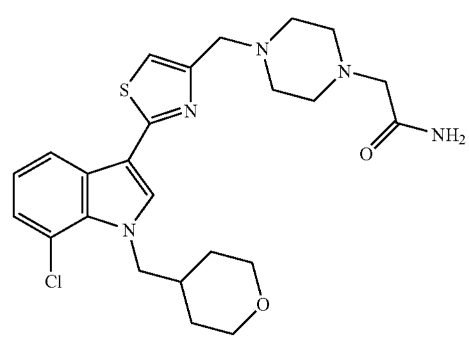 | 7.2 |

EXAMPLE 33

The Rat (Chung) Model of Neuropathic Pain

In this model, mechanical allodynia is induced by tight ligation of the left L5 spinal nerve. This assay has been employed successfully to demonstrate anti-allodynic effects of anticonvulsants (gabapentin), antidepressants (duloxetine) and opioid analgesics (morphine) which are used clinically in the treatment of neuropathic pain.

Male Wistar rats (150-175 g body weight at time of surgery) were employed in the study. Rats were placed on an elevated (~40 cm) mesh floor in perspex boxes and the rats' withdrawal threshold to a mechanical stimulus was measured using von Frey filaments of increasing force (2.6-167 mN) applied to the plantar surface of the paw using an up and down method (Chaplan S R et al., *J. Neurosci. Methods* 53: 55-63, 1994; Dixon J *Ann. Rev. Pharmacol. Toxicol.* 20: 441-462, 1980). Following baseline measurements each animal was anaesthetised and the L5 spinal nerve tightly ligated. The animals were allowed to recover from the surgery for a period of at least seven days. On the day of drug administration the paw withdrawal thresholds were re-measured (0 min). Immediately after this reading, the rats were dosed orally with vehicle or test compound. Readings were then made at 60, 120, 180 and 240 min after compound administration.

Data were expressed as mean ±s.e.m. The time of maximum effect for each animal in the top dose group was determined and these values averaged to calculate the mean time of maximum effect. For analytical purposes the time of maximum effect, $t_{max}$ was defined as the time point closest to this averaged value. Data at $t_{max}$ were compared between groups using the Kruskal-Wallis one-way analysis of variance, a non-parametric statistical test. Each of the treatment groups were then compared against the vehicle group, using the non-parametric Dunn's test. The ED$_{50}$ (dose at which allodynia is reversed by approximately 50%) value was also calculated at $t_{max}$ using non linear regression (sigmoidal dose response; variable slope) with constants of 0 and 15 g (cut-off) for the bottom and top, respectively (XLFit software).

What is claimed is:

1. An indole derivative having the general Formula I

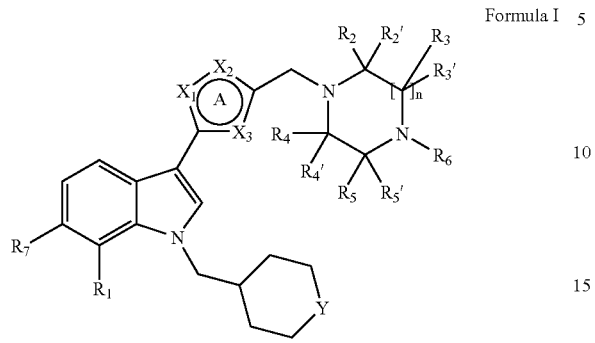

wherein
A represents a 5-membered aromatic heterocyclic ring, wherein $X_1$, $X_2$ and $X_3$ are independently selected from N, O, S and CH;
Y represents $CH_2$, O, S or $SO_2$;
$R_1$ is H, $(C_{1-4})$alkyl $(C_{1-4})$alkyloxy, CN or halogen;
$R_2$, $R_2'$, $R_3$, $R_3'$, $R_4$, $R_4'$, $R_5$ and $R_5'$ are independently hydrogen, $(C_{1-4})$alkyl (optionally substituted with OH) or CO—$OR_8$; or
one pair of geminal substituents $R_3$ and $R_3'$ or $R_5$ and $R_5'$ together represent a keto group, and the others are all hydrogen or $(C_{1-4})$alkyl; or
$R_2$ and $R_5$ together represent a methylene or an ethylene bridge, and $R_2'$, $R_3$, $R_3'$, $R_4$, $R_4'$ and $R_5'$ are hydrogen;
n is 1 or 2;
$R_6$ is H, $(C_{1-4})$alkyl (optionally substituted with OH, $(C_{1-4})$alkyloxy, CO—$NR_9R_{10}$, CO—$OR_{11}$ or 1,2,4-oxadiazol-3-yl), $SO_2NR_{12}R_{13}$ or $COOR_{14}$;
$R_7$ is H or halogen;
$R_8$ is $(C_{1-4})$alkyl;
$R_9$ and $R_{10}$ are independently hydrogen, $(C_{1-4})$alkyl or $(C_{3-7})$cycloalkyl, the alkyl groups being optionally substituted with OH or $(C_{1-4})$alkyloxy;
$R_{11}$ is H or $(C_{1-4})$alkyl;
$R_{12}$ and $R_{13}$ are independently H or $(C_{1-4})$alkyl;
$R_{14}$ is $(C_{1-6})$alkyl;
or a pharmaceutically acceptable salt thereof.

2. The indole derivative of claim 1, wherein the heterocyclic ring A represents 1,2,4-oxadiazole ($X_1$ is N, $X_2$ is O, $X_3$ is N) or 1,2,4-thiadiazole ($X_1$ is N, $X_2$ is S, $X_3$ is N).

3. The indole derivative of claim 1, wherein $R_1$ is Cl and $R_7$ is H.

4. The indole derivative of claim 1, wherein Y represents O.

5. The indole derivative of claim 1, wherein $R_6$ is $(C_{1-4})$alkyl, substituted with CO—$NR_9R_{10}$ or 1,2,4-oxadiazol-3-yl.

6. The indole derivative of claim 1, wherein $R_6$ is $CH_2$—$CONH_2$.

7. The indole derivative according to claim 1 which is selected from the group consisting of
3-({5-[4-(carbamoylmethyl)-piperazin-1-yl]methyl}-[1,2,4]-thiadiazol-3-yl)-7-chloro-1-(tetrahydropyran-4-yl)methyl-1H-indole;
7-chloro-3-({5-[4-(ethylcarbamoylmethyl)piperazin-1-yl]methyl}-[1,2,4]-thiadiazol-3-yl)-1-(tetrahydropyran-4-yl)methyl-1H-indole;
7-chloro-3-({5-[4-sulfamoylpiperazin-1-yl]methyl}-[1,2,4]-thiadiazol-3-yl)-1-(tetrahydropyran-4-yl)methyl-1H-indole;
7-ethyl-3-({5-[4-(N-isopropylcarbamoylmethyl)piperazin-1-yl]methyl}-[1,2,4]-thiadiazol-3-yl)-1-(tetrahydropyran-4-yl)methyl-1H-indole;
7-ethyl-3-({5-[4-(methoxycarbonylmethyl)piperazin-1-yl]methyl}-[1,2,4]-thiadiazol-3-yl)-1-(tetrahydropyran-4-yl)methyl-1H-indole;
3-({5-[4-(carbamoylmethyl)piperazin-1-yl]methyl}-[1,2,4]-thiadiazol-3-yl)-7-methoxy-1-(tetrahydropyran-4-yl)methyl-1H-indole;
3-({5-[4-(carbamoylmethyl)piperazin-1-yl]methyl}-[1,2,4]-thiadiazol-3-yl)-7-chloro-1-(1,1-dioxo-hexahydrothiopyran-4-yl)methyl-1H-indole;
3-({5-[4-(carbamoylmethyl)piperazin-1-yl]methyl}-[1,2,4]-oxadiazol-3-yl)-7-chloro-1-(tetrahydropyran-4-yl)methyl-1H-indole;
7-chloro-3-({5-[4-([1,2,4]-oxadiazol-3-ylmethyl)piperazin-1-yl]methyl}-[1,2,4]-oxadiazol-3-yl)-1-(1,1-dioxo-hexahydrothiopyran-4-yl)methyl-1H-indole;
3-[5-[4-(tert-butoxycarbonyl)-cis-2,6-dimethylpiperazin-1-ylmethyl]-[1,2,4]-oxadiazol-3-yl]-7-chloro-1-[(tetrahydropyran-4-yl)methyl]-1H-indole;
3-({5-[4-(carbamoylmethyl)homopiperazin-1-ylmethyl]-[1,2,4]-oxadiazol-3-yl}-7-chloro-1-[(tetrahydropyran-4-yl)methyl]-1H-indole;
(S)-7-chloro-3-[5-[3-hydroxymethyl-4-(methylcarbamoylmethyl)piperazin-1-ylmethyl]-[1,2,4]-oxadiazol-3-yl]-1-[(tetrahydropyran-4-yl)methyl]-1H-indole; and
3-({4-[4-(carbamoylmethyl)piperazin-1-yl]methyl}-[1,3]-thiazol-2-yl)-7-chloro-1-(tetra-hydropyran-4-yl)methyl-1H-indole, or a pharmaceutically acceptable salt thereof.

8. A pharmaceutical composition comprising an indole derivative of claim 1, or a pharmaceutically acceptable salt thereof, in admixture with pharmaceutically acceptable auxiliaries.

9. The pharmaceutical composition of claim 8, wherein an indole derivative is selected from the group consisting of
3-({5-[4-(carbamoylmethyl)-piperazin-1-yl]methyl}-[1,2,4]-thiadiazol-3-yl)-7-chloro-1-(tetrahydropyran-4-yl)methyl-1H-indole;
7-chloro-3-({5-[4-(ethylcarbamoylmethyl)piperazin-1-yl]methyl}-[1,2,4]-thiadiazol-3-yl)-1-(tetrahydropyran-4-yl)methyl-1H-indole;
7-chloro-3-({5-[4-sulfamoylpiperazin-1-yl]methyl}-[1,2,4]-thiadiazol-3-yl)-1-(tetrahydropyran-4-yl)methyl-1H-indole;
7-ethyl-3-({5-[4-(N-isopropylcarbamoylmethyl)piperazin-1-yl]methyl}-[1,2,4]-thiadiazol-3-yl)-1-(tetrahydropyran-4-yl)methyl-1H-indole;
7-ethyl-3-({5-[4-(methoxycarbonylmethyl)piperazin-1-yl]methyl}-[1,2,4]-thiadiazol-3-yl)-1-(tetrahydropyran-4-yl)methyl-1H-indole;
3-({5-[4-(carbamoylmethyl)piperazin-1-yl]methyl}-[1,2,4]-thiadiazol-3-yl)-7-methoxy-1-(tetrahydropyran-4-yl)methyl-1H-indole;
3-({5-[4-(carbamoylmethyl)piperazin-1-yl]methyl}-[1,2,4]-thiadiazol-3-yl)-7-chloro-1-(1,1-dioxo-hexahydrothiopyran-4-yl)methyl-1H-indole;
3-({5-[4-(carbamoylmethyl)piperazin-1-yl]methyl}-[1,2,4]-oxadiazol-3-yl)-7-chloro-1-(tetrahydropyran-4-yl)methyl-1H-indole;
7-chloro-3-({5-[4-([1,2,4]-oxadiazol-3-ylmethyl)piperazin-1-yl]methyl}-[1,2,4]-oxadiazol-3-yl)-1-(1,1-dioxo-hexahydrothiopyran-4-yl)methyl-1H-indole;
3-[5-[4-(tert-butoxycarbonyl)-cis-2,6-dimethylpiperazin-1-ylmethyl]-[1,2,4]-oxadiazol-3-yl]-7-chloro-1-[(tetrahydropyran-4-yl)methyl]-1H-indole;

3-({5-[4-(carbamoylmethyl)homopiperazin-1-ylmethyl]-[1,2,4]-oxadiazol-3-yl}-7-chloro-1-[(tetrahydropyran-4-yl)methyl]-1H-indole;

(S)-7-chloro-3-[5-[3-hydroxymethyl-4-(methylcarbamoylmethyl)piperazin-1-ylmethyl]-[1,2,4]-oxadiazol-3-yl]-1-[(tetrahydropyran-4-yl)methyl]-1H-indole; and 3-({4-[4-(carbamoylmethyl)piperazin-1-yl]methyl}-[1,3]-thiazol-2-yl)-7-chloro-1-(tetra-hydropyran-4-yl)methyl-1H-indole, or a pharmaceutically acceptable salt thereof.

10. A method for the treatment of pain in a patient in need thereof, the method comprising administering to the patient a therapeutically effective amount of an indole derivative of claim 1 or a pharmaceutically acceptable salt thereof.

11. The method of claim 10, wherein the indole derivative is selected from the group consisting of 3-({5-[4-(carbamoylmethyl)-piperazin-1-yl]methyl}-[1,2,4]-thiadiazol-3-yl)-7-chloro-1-(tetrahydropyran-4-yl)methyl-1H-indole;

7-chloro-3-({5-[4-(ethylcarbamoylmethyl)piperazin-1-yl]methyl}-[1,2,4]-thiadiazol-3-yl)-1-(tetrahydropyran-4-yl)methyl-1H-indole;

7-chloro-3-({5-[4-sulfamoylpiperazin-1-yl]methyl}-[1,2,4]-thiadiazol-3-yl)-1-(tetrahydropyran-4-yl)methyl-1H-indole;

7-ethyl-3-({5-[4-(N-isopropylcarbamoylmethyl)piperazin-1-yl]methyl}-[1,2,4]-thiadiazol-3-yl)-1-(tetrahydropyran-4-yl)methyl-1H-indole;

7-ethyl-3-({5-[4-(methoxycarbonylmethyl)piperazin-1-yl]methyl}-[1,2,4]-thiadiazol-3-yl)-1-(tetrahydropyran-4-yl)methyl-1H-indole;

3-({5-[4-(carbamoylmethyl)piperazin-1-yl]methyl}-[1,2,4]-thiadiazol-3-yl)-7-methoxy-1-(tetrahydropyran-4-yl)methyl-1H-indole;

3-({5-[4-(carbamoylmethyl)piperazin-1-yl]methyl}-[1,2,4]-thiadiazol-3-yl)-7-chloro-1-(1,1-dioxo-hexahydrothiopyran-4-yl)methyl-1H-indole;

3-({5-[4-(carbamoylmethyl)piperazin-1-yl]methyl}-[1,2,4]-oxadiazol-3-yl)-7-chloro-1-(tetrahydropyran-4-yl)methyl-1H-indole;

7-chloro-3-({5-[4-([1,2,4]-oxadiazol-3-ylmethyl)piperazin-1-yl]methyl}-[1,2,4]-oxadiazol-3-yl)-1-(1,1-dioxo-hexahydrothiopyran-4-yl)methyl-1H-indole;

3-[5-[4-(tert-butoxycarbonyl)-cis-2,6-dimethylpiperazin-1-ylmethyl]-[1,2,4]-oxadiazol-3-yl]-7-chloro-1-[(tetrahydropyran-4-yl)methyl]-1H-indole;

3-{5-[4-(carbamoylmethyl)homopiperazin-1-ylmethyl]-[1,2,4]-oxadiazol-3-yl}-7-chloro-1-[(tetrahydropyran-4-yl)methyl]-1H-indole;

(S)-7-chloro-3-[5-[3-hydroxymethyl-4-(methylcarbamoylmethyl)piperazin-1-ylmethyl]-[1,2,4]-oxadiazol-3-yl]-1-[(tetrahydropyran-4-yl)methyl]-1H-indole; and 3-({4-[4-(carbamoylmethyl)piperazin-1-yl]methyl}-[1,3]-thiazol-2-yl)-7-chloro-1-(tetra-hydropyran-4-yl)methyl-1H-indole, or a pharmaceutically acceptable salt thereof.

12. The method of claim 10, wherein is selected from the group consisting of peri-operative pain, chronic pain, neuropathic pain, cancer pain and pain and spasticity associated with multiple sclerosis.

13. 3-({5-[4-(Carbamoylmethyl)piperazin-1-yl]methyl}-[1,2,4]-oxadiazol-3-yl)-7-chloro-1-(tetrahydropyran-4-yl) methyl-1H-indole or a pharmaceutically acceptable salt thereof.

14. A pharmaceutical composition comprising an indole derivative of claim 13, or a pharmaceutically acceptable salt thereof, in admixture with pharmaceutically acceptable auxiliaries.

15. A method for the treatment of pain in a patient in need thereof, the method comprising administering to the patient a therapeutically effective amount of the indole derivative of claim 13 or a pharmaceutically acceptable salt thereof.

16. The method of claim 15, wherein the pain is selected from the group consisting of pen-operative pain, chronic pain, neuropathic pain, cancer pain and pain and spasticity associated with multiple sclerosis.

17. The method of claim 16, wherein the pain is pen-operative pain.

18. The method of claim 16, wherein the pain is chronic pain.

19. The method of claim 16, wherein the pain is neuropathic pain.

20. The method of claim 16, wherein the pain is cancer pain.

21. The method of claim 16, wherein the pain is pain and spasticity associated with multiple sclerosis.

\* \* \* \* \*